(12) United States Patent
Murphy et al.

(10) Patent No.: US 9,636,109 B2
(45) Date of Patent: May 2, 2017

(54) BIOLOGICALLY ACTIVE SUTURES FOR REGENERATIVE MEDICINE

(75) Inventors: William L. Murphy, Madison, WI (US); Jae Sung Lee, Madison, WI (US); Mark D. Markel, Middleton, WI (US); Ben K. Graf, Madison, WI (US); Geoffrey Baer, Madison, WI (US); Yan Lu, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1147 days.

(21) Appl. No.: 12/507,635

(22) Filed: Jul. 22, 2009

(65) Prior Publication Data

US 2011/0022085 A1    Jan. 27, 2011

(51) Int. Cl.
| | |
|---|---|
| *A61B 17/04* | (2006.01) |
| *A61B 17/06* | (2006.01) |
| *A61L 27/32* | (2006.01) |
| *A61L 27/54* | (2006.01) |
| *A61L 27/58* | (2006.01) |
| *A61L 29/10* | (2006.01) |
| *A61L 29/14* | (2006.01) |
| *A61L 29/16* | (2006.01) |
| *A61L 31/08* | (2006.01) |
| *A61L 31/14* | (2006.01) |
| *A61L 31/16* | (2006.01) |

(Continued)

(52) U.S. Cl.
CPC ...... *A61B 17/06166* (2013.01); *A61L 17/005* (2013.01); *A61L 17/06* (2013.01); *A61L 17/145* (2013.01); *A61L 27/32* (2013.01); *A61L 27/54* (2013.01); *A61L 27/58* (2013.01); *A61L 29/106* (2013.01); *A61L 29/148* (2013.01); *A61L 29/16* (2013.01); *A61L 31/086* (2013.01); *A61L 31/148* (2013.01); *A61L 31/16* (2013.01); *A61B 2017/00889* (2013.01); *A61B 2017/00893* (2013.01)

(58) Field of Classification Search
CPC .... A61B 17/06166; A61B 2017/00893; A61B 2017/00889
USPC ................... 606/228, 230; 428/357
See application file for complete search history.

(56) References Cited

U.S. PATENT DOCUMENTS 4,185,637 A * 1/1980 Mattei ........................... 606/230
4,201,216 A * 5/1980 Mattei ........................... 606/230
(Continued)

OTHER PUBLICATIONS

Murphy, et al., "Healing of Bone and Connective Tissues," in Encyclopedia of Biomaterials and Biomedical Engineering, Wnek, G.B., ed., Informa Healthcare, 2006.

(Continued)

*Primary Examiner* — Todd J Scherbel
*Assistant Examiner* — Son Dang
(74) *Attorney, Agent, or Firm* — Stinson Leonard Street LLP

(57) ABSTRACT

The present disclosure generally relates to biodegradable and bioresorbable materials having a mineral layer on the surface of the material. More particularly, the disclosure relates to biodegradable and bioresorbable orthopedic devices having a degradable mineral layer on the surface thereof that can be used as a delivery vehicle for biological substances. Also provided are various methods of using the mineralized devices in tissue regeneration, including bone tissue engineering, and methods for producing the mineralized devices.

10 Claims, 17 Drawing Sheets

(51) Int. Cl.
*A61L 17/00* (2006.01)
*A61L 17/06* (2006.01)
*A61L 17/14* (2006.01)
*A61B 17/00* (2006.01)

(56) References Cited

U.S. PATENT DOCUMENTS

| | | | | |
|---|---|---|---|---|
| 4,983,180 | A * | 1/1991 | Kawai et al. | 606/230 |
| 5,067,959 | A * | 11/1991 | Korthoff | 606/224 |
| 6,045,571 | A * | 4/2000 | Hill et al. | 606/228 |
| 6,716,234 | B2 * | 4/2004 | Grafton et al. | 606/228 |
| 6,767,928 | B1 | 7/2004 | Murphy et al. | |
| 7,329,271 | B2 * | 2/2008 | Koyfman et al. | 606/228 |
| 8,012,172 | B2 * | 9/2011 | Grafton et al. | 606/228 |
| 2002/0151617 | A1 | 10/2002 | Mao | |
| 2002/0187104 | A1 | 12/2002 | Li et al. | |
| 2004/0162580 | A1 | 8/2004 | Hain | |
| 2005/0063941 | A1 | 3/2005 | Bezemer et al. | |
| 2005/0149119 | A1 * | 7/2005 | Koyfman et al. | 606/228 |
| 2006/0002970 | A1 * | 1/2006 | Aspenberg | A61B 17/06166 424/423 |
| 2007/0016307 | A1 * | 1/2007 | Zimmermann et al. | 623/23.75 |
| 2007/0112385 | A1 * | 5/2007 | Conlon | 606/232 |
| 2008/0255612 | A1 * | 10/2008 | Hunter | 606/228 |
| 2009/0087472 | A1 | 4/2009 | Murphy et al. | |
| 2009/0226500 | A1 * | 9/2009 | Avelar et al. | 424/423 |

OTHER PUBLICATIONS

Kohno, et al., "Immunohistochemical demonstration of growth factors at the tendon-bone interface in anterior cruciate ligament reconstruction using a rabbit model," J. Orthop. Sci., 2007, vol. 12(1) p. 67-73.

Rodeo, et al., "Use of recombinant human bone morphogenetic protein-2 to enhance tendon healing in a bone tunnel," Am. J. Sports Med., 1999, vol. 27 (4), p. 476-88.

Yoshikawa, et al., "Effects of local administration of vascular endothelial growth factor on mechanical characteristics of the semitendinosus tendon graft after anterior cruciate ligament reconstruction in sheep," Am. J. Sports Med., 2006, vol. 34(12), p. 1918-25.

Murphy, et al., J. Am. Chem. Soc., 2002, vol. 124, p. 1910-1917.

Min Lu, et al., "Partitioning of proteins and thylakoid membrane vesicles in aqueous two-phase systems with hydrophobically modified dextran," Journal of Chromatography A, 1994, vol. 668, pp. 215-228.

Helal, R., et al., "Determination of lysozyme activity by a fluorescence technique in comparison with the classical turbidity assay," Pharmazie, 2008, vol. 63, pp. 415-419.

Jongpaiboonkit et al., "Mineral-Coated Polymer Microspheres for Controlled Protein Binding and Release", Advanced Materials, 2009, 21, pp. 1-4.

Murphy, W. L.; Hsiong, S.; Richardson, T. P.; Simmons, C. A.; Mooney, D. J., Effects of a bone-like mineral film on phenotype of adult human mesenchymal stem cells in vitro. Biomaterials 2005, 26, (3), 303-10.

Murphy, W. L.; Kohn, D. H.; Mooney, D. J., Growth of continuous bonelike mineral within porous poly(lactide-co-glycolide) scaffolds in vitro. J Biomed Mater Res 2000, 50, (1), 50-8.

Murphy, W. L.; Mercurius, K. O.; Koide, S.; Mrksich, M., Substrates for cell adhesion prepared via active site-directed immobilization of a protein domain. Langmuir 2004, 20, (4), 1026-1030.

Murphy, W. L.; Mooney, D. J., Molecular-scale biomimicry. Nat Biotechnol 2002, 20, (1), 30-1.

Lu, Y.; Markel, M. D.; Nemke, B.; Lee, J. S.; Graf, B. K.; Murphy, W. L., Influence of hydroxyapatite-coated growth factor-releasing interference screws on tendon-bone healing in an ovine model. Arthroscopy 2009, 25, (12), 1427-1435.

Murphy, W. L.; Dillmore, W. S.; Modica, J.; Mrksich, M., Dynamic hydrogels: translating a protein conformational change into macroscopic motion. Angew Chem Int Ed Engl 2007, 46, (17), 3066-9.

Murphy, W. L.; Mooney, D. J., Controlled delivery of inductive proteins, plasmid DNA and cells from tissue engineering matrices. J Periodontal Res 1999, 34, (7), 413-419.

Richardson, T. P.; Murphy, W. L.; Mooney, D. J., Polymeric delivery of proteins and plasmid DNA for tissue engineering and gene therapy. Crit Rev Eukaryot Gene Expr 2001, 11, (1-3), 47-58.

Richardson, T. P.; Murphy, W. L.; Mooney, D. J., Selective adipose tissue ablation by localized, sustained drug delivery. Plast Reconstr Surg 2003, 112, (1), 162-70.

Fazan, F.; Marquis, P., Dissolution behavior of plasma-sprayed hydroxyapatite coatings. Journal of Materials Science—Materials in Medicine 2000, 11, (12), 787-792.

Lin, J.; Kuo, K.; Ding, S.; Ju, C., Surface reaction of stoichiometric and calcium-deficient hydroxyapatite in simulated body fluid. Journal of Materials Science—Materials in Medicine 2001, 12, (8), 731-741.

Driessens, F. C.; van Dijk, J. W.; Borggreven, J. M., Biological calcium phosphates and their role in the physiology of bone and dental tissues I. Composition and solubility of calcium phosphates. Calcif Tissue Res 1978, 26, (2), 127-37.

Bunker, B. C., Rieke, P.C., Tarasevich, B.J., Campbell, A.A., Fryxell, G.E., Graff, G.L., Song, L., Liu, J., Virden, W., McVay, G.L., Ceramic thin film formation on functionalized interfaces through biomimetic processing. Science 1994, 264, 48-55.

Hjerten, S.; Levin, O.; Tiselius, A., Protein chromatography on calcium phosphate columns. Arch Biochem Biophys 1956, 65, (1), 132-55.

Schroder, E.; Jonsson, T.; Poole, L., Hydroxyapatite chromatography: altering the phosphate-dependent elution profile of protein as a function of pH. Anal Biochem 2003, 313, (1), 176-8.

Matsumoto, T.; Okazaki, M.; Inoue, M.; Yamaguchi, S.; Kusunose, T.; Toyonaga, T.; Hamada, Y.; Takahashi, J., Hydroxyapatite particles as a controlled release carrier of protein. Biomaterials 2004, 25, (17), 3807-12.

Centrella, M.; McCarthy, T. L.; Canalis, E., Skeletal tissue and transforming growth factor beta. Faseb J 1988, 2, (15), 3066-73.

Gorski, J. P., Is all bone the same? Distinctive distributions and properties of non-collagenous matrix proteins in lamellar vs. woven bone imply the existence of different underlying osteogenic mechanisms. Crit Rev Oral Biol Med 1998, 9, (2), 201-23.

Gorski, J. P.; Griffin, D.; Dudley, G.; Stanford, C.; Thomas, R.; Huang, C.; Lai, E.; Karr, B.; Solursh, M., Bone acidic glycoprotein-75 is a major synthetic product of osteoblastic cells and localized as 75- and/or 50-kDa forms in mineralized phases of bone and growth plate and in serum. J Biol Chem 1990, 265, (25), 14956-63.

Peret, B. J.; Murphy, W. L., Controllable soluble protein concentration gradients in hydrogel networks. Advanced Functional Materials 2008, 18, 3410-3417.

Murphy, W.; Mooney, D., Biomineralization via bioinspired variation in polymer surface chemistry. Abstracts of Papers of the American Chemical Society 2001, 222, U344.

Ngankam, P. A., Lavalle, P., Voegel, J.C., et al., Influence of polyelectrolyte multilayer films on calcium phosphate nucleation. Journal of the American Chemical Society 2000, 122, 8998-9005.

Fazan, F.; Marquis, P. M., Dissolution behavior of plasma-sprayed hydroxyapatite coatings. J Mater Sci Mater Med 2000, 11, (12), 787-92.

Lin, J. H.; Kuo, K. H.; Ding, S. J.; Ju, C. P., Surface reaction of stoichiometric and calcium-deficient hydroxyapatite in simulated body fluid. J Mater Sci Mater Med 2001, 12, (8), 731-41.

Taguchi, T.; Kishida, A.; Akashi, M., Apatite formation on/in hydrogel matrices using an alternate soaking process: II. Effect of swelling ratios of poly(vinyl alcohol) hydrogel matrices on apatite formation. J Biomater Sci Polym Ed 1999, 10, (3), 331-9.

Taguchi, T.; Shiraogawa, M.; Kishida, A.; Akashi, M., A study on hydroxyapatite formation on/in the hydroxyl groups-bearing nonionic hydrogels. J Biomater Sci Polym Ed 1999, 10, (1), 19-32.

ASTM Standard C633-79: Standard test method for adhesion or cohesive strength of flame-sprayed coatings. In; ASTM: 1993; pp. 652-656.

(56) References Cited

OTHER PUBLICATIONS

Sun, L.; Berndt, C. C.; Gross, K. A.; Kucuk, A., Material fundamentals and clinical performance of plasma-sprayed hydroxyapatite coatings: a review. J Biomed Mater Res 2001, 58, (5), 570-92.

Murphy, W.; Messersmith, P., Compartmental control of mineral formation: adaptation of a biomineralization strategy for biomedical use. Polyhedron 2000, 19, (3), 357-363.

Elliott, J., Structure and Chemistry of Apatites and other Calcium Orthophosphates. Elsevier: Amsterdam, 1994.

Leung, D. W.; Cachianes, G.; Kuang, W. J.; Goeddel, D. V.; Ferrara, N., Vascular endothelial growth factor is a secreted angiogenic mitogen. Science 1989, 246, (4935), 1306-9.

Petryk, A.; Shimmi, O.; Jia, X.; Carlson, A. E.; Tervonen, L.; Jarcho, M. P.; O'Connor M, B.; Gopalakrishnan, R., Twisted gastrulation and chordin inhibit differentiation and mineralization in MC3T3-E1 osteoblast-like cells. Bone 2005, 36, (4), 617-26.

Lee, Y. C.; Yang, D., Determination of lysozyme activities in a microplate format. Anal Biochem 2002, 310, (2), 223-4.

Raiche, A. T.; Puleo, D. A., Modulated release of bioactive protein from multilayered blended PLGA coatings. Int J Pharm 2006, 311, (1-2), 40-9.

Lu, Y.; Markel, M. D.; Nemke, B.; Wynn, S.; Graf, B. K., Comparison of Single vs. Double-Tunnel Tendon-to-Bone Healing in an Ovine Model: A Biomechanical and Histological Analysis. Am J Sports Med 2009, 37, (3), 512-517.

Barber, F. A.; Herbert, M. A.; Coons, D. A.; Boothby, M. H., Sutures and suture anchors—update 2006. Arthroscopy 2006, 22, (10), 1063-69.

Wright, P. B.; Budoff, J. E.; Yeh, M. L.; Kelm, Z. S.; Luo, Z. P., Strength of damaged suture: an in vitro study. Arthroscopy 2006, 22, (12), 1270-1275 e3.

Wust, D. M.; Meyer, D. C.; Favre, P.; Gerber, C., Mechanical and handling properties of braided polyblend polyethylene sutures in comparison to braided polyester and monofilament polydioxanone sutures. Arthroscopy 2006, 22, (11), 1146-53.

Bodde, E. W.; Wolke, J. G.; Kowalski, R. S.; Jansen, J. A., Bone regeneration of porous beta-tricalcium phosphate (Conduit TCP) and of biphasic calcium phosphate ceramic (Biosel) in trabecular defects in sheep. J Biomed Mater Res A 2007, 82, (3), 711-22.

Rodeo, S.; Kawamura, S.; Ma, C.; Deng, X.; Sussman, P.; Hays, P.; Ying, L., The effect of osteoclastic activity on tendon-to-bone healing: An experimental study in rabbits. Journal of Bone and Joint Surgery—American vol. 2007, 89A, (10), 2250-2259.

Frisch, T.; Sorensen, M. S.; Overgaard, S.; Lind, M.; Bretlau, P., Volume-referent bone turnover estimated from the interlabel area fraction after sequential labeling. Bone 1998, 22, (6), 677-82.

Miller, S. C.; Pan, H.; Wang, D.; Bowman, B. M.; Kopeckova, P.; Kopecek, J., Feasibility of using a bone-targeted, macromolecular delivery system coupled with prostaglandin E(1) to promote bone formation in aged, estrogen-deficient rats. Pharm Res 2008, 25, (12), 2889-95.

Aro, H. T.; Markel, M. D.; Chao, E. Y., Cortical bone reactions at the interface of external fixation half-pins under different loading conditions. J Trauma 1993, 35, (5), 776-85.

Markel, M. D.; Wikenheiser, M. A.; Chao, E. Y., A study of fracture callus material properties: relationship to the torsional strength of bone. J Orthop Res 1990, 8, (6), 843-50.

Markel, M. D.; Wikenheiser, M. A.; Chao, E. Y., Formation of bone in tibial defects in a canine model. Histomorphometric and biomechanical studies. J Bone Joint Surg Am 1991, 73, (6), 914-23.

Zabka, A.; Pluhar, G.; Edwards, R.; Manley, P.; Hayashi, K.; Heiner, J.; Kalscheur, V.; Seeherman, H.; Markel, M., Histomorphometric description of allograft bone remodeling and union in a canine segmental femoral defect model: a comparison of rhBMP-2, cancellous bone graft, and absorbable collagen sponge. Journal of Orthopaedic Research 2001, 19, (2), 318-327.

Edwards, R.; Seeherman, H.; Bogdanske, J.; Devitt, J.; Vanderby, P.; Markel, M., Percutaneous injection of recombinant human bone morphogenetic protein-2 in a calcium phosphate paste accelerates healing of a canine tibial osteotomy. Journal of Bone and Joint Surgery—American vol. 2004, 86A, (7), 1425-1438.

Walsh, W. R.; Cotton, N. J.; Stephens, P.; Brunelle, J. E.; Langdown, A.; Auld, J.; Vizesi, F.; Bruce, W., Comparison of poly-L-lactide and polylactide carbonate interference screws in an ovine anterior cruciate ligament reconstruction model. Arthroscopy 2007, 23, (7), 757-65, 765 e1-2.

International Search Report and Written Opinion for PCT/US2010/042312, dated Nov. 4, 2010.

Crane, G. M.; Ishaug, S. L.; Mikos, A. G., Bone tissue engineering. Nat Med 1995, 1, (12), 1322-4.

Mann, S.; Ozin, G.A., Synthesis of inorganic materials with complex form. Nature 1996, 382, 313-318.

Statistics, N. C. f. H., Ambulatory and inpatient procedures according to place, sex, age, and type of procedure: United States, 1994-1998. U.S. Department of Health and Human Services: Hyattsville, MD, 2000.

Sarikaya, M., Biomimetics: materials fabrication through biology. Proc Natl Acad Sci U S A 1999, 96, (25), 14183-5.

Linn, R. M.; Fischer, D. A.; Smith, J. P.; Burstein, D. B.; Quick, D. C., Achilles tendon allograft reconstruction of the anterior cruciate ligament-deficient knee. Am J Sports Med 1993, 21, (6), 825-31.

Buelow, J. U.; Siebold, R.; Ellermann, A., A new bicortical tibial fixation technique in anterior cruciate ligament reconstruction with quadruple hamstring graft. Knee Surg Sports Traumatol Arthrosc 2000, 8, (4), 218-25.

Kimura, Y.; Hokugo, A.; Takamoto, T.; Tabata, Y.; Kurosawa, H., Regeneration of anterior cruciate ligament by biodegradable scaffold combined with local controlled release of basic fibroblast growth factor and collagen wrapping. Tissue Eng Part C Methods 2008, 14, (1), 47-57.

Demirag, B.; Sarisozen, B.; Ozer, O.; Kaplan, T.; Ozturk, C., Enhancement of tendon-bone healing of anterior cruciate ligament grafts by blockage of matrix metalloproteinases. J Bone Joint Surg Am 2005, 87, (11), 2401-10.

Saltzman, W. M.; Olbricht, W. L., Building drug delivery into tissue engineering. Nat Rev Drug Discov 2002, 1, (3), 177-86.

Cohen, S.; Yoshioka, T.; Lucarelli, M.; Hwang, L. H.; Langer, R., Controlled delivery systems for proteins based on poly(lactic/glycolic acid) microspheres. Pharm Res 1991, 8, (6), 713-20.

Langer, R., New methods of drug delivery. Science 1990, 249, (4976), 1527-33.

Langer, R.; Folkman, J., Polymers for the sustained release of proteins and other macromolecules. Nature 1976, 263, (5580), 797-800.

Langer, R.; Moses, M., Biocompatible controlled release polymers for delivery of polypeptides and growth factors. J Cell Biochem 1991, 45, (4), 340-5.

Leong, K. W.; Kost, J.; Mathiowitz, E.; Langer, R., Polyanhydrides for controlled release of bioactive agents. Biomaterials 1986, 7, (5), 364-71.

Pekarek, K. J.; Jacob, J. S.; Mathiowitz, E., Double-walled polymer microspheres for controlled drug release. Nature 1994, 367, (6460), 258-60.

Lee, K. Y.; Peters, M. C.; Anderson, K. W.; Mooney, D. J., Controlled growth factor release from synthetic extracellular matrices. Nature 2000, 408, (6815), 998-1000.

Tabata, Y.; Ikada, Y., Vascularization effect of basic fibroblast growth factor released from gelatin hydrogels with different biodegradabilities. Biomaterials 1999, 20, (22), 2169-75.

Sullivan, F. a., U.S. Drug Delivery Technology Markets. Frost and Sullivan: 2001.

Murphy, W. L.; Peters, M. C.; Kohn, D. H.; Mooney, D. J., Sustained release of vascular endothelial growth factor from mineralized poly(lactide-co-glycolide) scaffolds for tissue engineering. Biomaterials 2000, 21, (24), 2521-7.

Murphy, W. L.; Simmons, C. A.; Kaigler, D.; Mooney, D. J., Bone regeneration via a mineral substrate and induced angiogenesis. J Dent Res 2004, 83, (3), 204-10.

Sheridan, M. H.; Shea, L. D.; Peters, M. C.; Mooney, D. J., Bioabsorbable polymer scaffolds for tissue engineering capable of sustained growth factor delivery. J Control Release 2000, 64, (1-3), 91-102.

(56) References Cited

OTHER PUBLICATIONS

Howdle, S. M. W., M.S.; Whitaker, M.J.; Popov, M.C.; Davies, M.C.; Mandel, F.S.; Wang, J.D.; Shakesheff, K.M., Supercritical fluid mixing: preparation of thermally sensitive polymer composites containing bioactive materials. Chemical Communications 2001, 1, (109-110).

Yang, X. B.; Green, D. W.; Roach, H. I.; Clarke, N. M.; Anderson, H. C.; Howdle, S. M.; Shakesheff, K. M.; Oreffo, R. O., Novel osteoinductive biomimetic scaffolds stimulate human osteoprogenitor activity—implications for skeletal repair. Connect Tissue Res 2003, 44 Suppl 1, 312-7.

Richardson, T. P.; Peters, M. C.; Ennett, A. B.; Mooney, D. J., Polymeric system for dual growth factor delivery. Nat Biotechnol 2001, 19, (11), 1029-34.

Zisch, A. H.; Schenk, U.; Schense, J. C.; Sakiyama-Elbert, S. E.; Hubbell, J. A., Covalently conjugated VEGF—fibrin matrices for endothelialization. J Control Release 2001, 72, (1-3), 101-13.

Raiche, A. T.; Puleo, D. A., Cell responses to BMP-2 and IGF-I released with different time-dependent profiles. J Biomed Mater Res 2004, 69A, (2), 342-50.

Raiche, A. T.; Puleo, D. A., In vitro effects of combined and sequential delivery of two bone growth factors. Biomaterials 2004, 25, (4), 677-85.

Alt, V.; Pfefferle, H. J.; Kreuter, J.; Stahl, J. P.; Pavlidis, T.; Meyer, C.; Mockwitz, J.; Wenisch, S.; Schnettler, R., Effect of glycerol-L-lactide coating polymer on bone ingrowth of bFGF-coated hydroxyapatite implants. J Control Release 2004, 99, (1), 103-11.

Mann, S., Archibald, D.D., Didymus, J.M., et al., Crystallization and inorganic-organic interfaces—biominerals and biomimetic synthesis. Science 1993, 261, 1286-1292.

Hossain, M.; Irwin, R.; Baumann, M. J.; McCabe, L. R., Hepatocyte growth factor (HGF) adsorption kinetics and enhancement of osteoblast differentiation on hydroxyapatite surfaces. Biomaterials 2005, 26, (15), 2595-602.

Liu, Y.; Hunziker, E. B.; Layrolle, P.; De Bruijn, J. D.; De Groot, K., Bone morphogenetic protein 2 incorporated into biomimetic coatings retains its biological activity. Tissue Eng 2004, 10, (1-2), 101-8.

Ripamonti, U.; Yeates, L.; van den Heever, B., Initiation of heterotopic osteogenesis in primates after chromatographic adsorption of osteogenin, a bone morphogenetic protein, onto porous hydroxyapatite. Biochem Biophys Res Commun 1993, 193, (2), 509-17.

Sumner, D. R.; Turner, T. M.; Urban, R. M.; Virdi, A. S.; Inoue, N., Additive enhancement of implant fixation following combined treatment with rhTGF-beta2 and rhBMP-2 in a canine model. J Bone Joint Surg Am 2006, 88, (4), 806-17.

Zambonin, G.; Grano, M.; Greco, G.; Oreffo, R. O.; Triffit, J. T., Hydroxyapatite coated with insulin-like growth factor 1 (IGF1) stimulates human osteoblast activity in vitro. Acta Orthop Scand 1999, 70, (2), 217-20.

Bajpai, P. K.; Benghuzzi, H. A., Ceramic systems for long-term delivery of chemicals and biologicals. J Biomed Mater Res 1988, 22, (12), 1245-66.

Feng, B.; Chen, J.; Zhang, X., Interaction of calcium and phosphate in apatite coating on titanium with serum albumin. Biomaterials 2002, 23, (12), 2499-507.

Zeng, H.; Chittur, K. K.; Lacefield, W. R., Analysis of bovine serum albumin adsorption on calcium phosphate and titanium surfaces. Biomaterials 1999, 20, (4), 377-84.

Zhang, R.; Xu, D.; Landeryou, T.; Toth, C.; Dimaano, N.; Berry, J.; Evans, J.; Hawkins, M., Ectopic bone formation using osteogenic protein-1 carried by a solution precipitated hydroxyapatite. J Biomed Mater Res A 2004, 71, (3), 412-8.

Liu, Y.; Hunziker, E. B.; Randall, N. X.; de Groot, K.; Layrolle, P., Proteins incorporated into biomimetically prepared calcium phosphate coatings modulate their mechanical strength and dissolution rate. Biomaterials 2003, 24, (1), 65-70.

Luong, L. N.; Hong, S. I.; Patel, R. J.; Outslay, M. E.; Kohn, D. H., Spatial control of protein within biomimetically nucleated mineral. Biomaterials 2006, 27, (7), 1175-86.

Yu, X.; Qu, H.; Knecht, D. A.; Wei, M., Incorporation of bovine serum albumin into biomimetic coatings on titanium with high loading efficacy and its release behavior. J Mater Sci Mater Med 2009, 20, (1), 287-94.

Azevedo, H.; Leonor, I.; Alves, C.; Reis, R., Incorporation of proteins and enzymes at different stages of the preparation of calcium phosphate coatings on a degradable substrate by a biomimetic methodology. Materials Science & Engineering C 2005, 25, (2), 169-179.

Jayasuriya, A. C.; Shah, C., Controlled release of insulin-like growth factor-1 and bone marrow stromal cell function of bone-like mineral layer-coated poly(lactic-co-glycolic acid) scaffolds. J Tissue Eng Regen Med 2008, 2, (1), 43-9.

Leonor, I.; Azevedo, H.; Reis, R., Effects of protein incorporation on calcium phosphate coating. Materials Science & Engineering C 2009, pp. 913-918.

Liu, Y.; de Groot, K.; Hunziker, E. B., Osteoinductive implants: the mise-en-scene for drug-bearing biomimetic coatings. Ann Biomed Eng 2004, 32, (3), 398-406.

Sogo, Y.; Ito, A.; Onoguchi, M.; Oyane, A.; Tsurushima, H.; Ichinose, N., Formation of a FGF-2 and calcium phosphate composite layer on a hydroxyapatite ceramic for promoting bone formation. Biomed Mater 2007, 2, (3), S175-80.

Lowenstam, H. A., Weiner, S., On Biomineralization. Oxford University Press: Oxford, 1989.

Blom, E.J., et al., "Transforming growth factor-β1 incorporation in a calcium phosphate bone cement: Material properties and release characteristics," J Biomed Mater Res 59: 265-272, 2002.

William L. Murphy et al., "Bioinspired Growth of Crystalline Carbonate Apatite on Biodegradable Polymer Substrata," Journal of the American Chemical Society, vol. 124, No. 9, Mar. 1, 2002, pp. 1910-1917.

* cited by examiner

- ● Cytochrome c (mineralized suture)
- ▼ Lysozyme (mineralized suture)
- ○ Cytochrome c (non-mineralized suture)
- ▽ Lysozyme (non-mineralized suture)

Fluorescein-labeled BSA

Rhodamine-labeled lysozyme

BIOLOGICALLY ACTIVE SUTURES FOR REGENERATIVE MEDICINE

STATEMENT REGARDING FEDERALLY SPONSORED RESEARCH OR DEVELOPMENT

This invention was made with United States Government support awarded by the following agency: NIH AR052893. The United States Government has certain rights in this invention.

BACKGROUND OF THE DISCLOSURE

The present disclosure generally relates to biodegradable and bioresorbable materials having a mineral layer on the surface of the material. More particularly, the disclosure relates to biodegradable and bioresorbable orthopedic devices having a degradable mineral layer on the surface thereof that can be used as a delivery vehicle for biological substances. Also provided are various methods of using the mineralized devices in tissue regeneration, including bone tissue engineering, and methods for producing the mineralized devices.

The field of orthopedic tissue engineering has developed rapidly in response to the expanding need for skeletal tissue replacements to treat injury, disease, and birth defects. Costs of musculoskeletal conditions represent an average of 3% of the gross domestic product of developed countries, an estimated $254 billion annually in the United States, and bone and joint diseases account for half of all chronic conditions in people over the age of 50. The predicted doubling of this age group's population by 2020 suggests that the tremendous need for novel bone repair and replacement therapies will continue to grow rapidly. Bone-tendon healing presents a particularly challenging problem that must be addressed in myriad orthopedic applications, including cruciate ligament reconstruction, rotator cuff repair, patellar tendon repair, and avulsion injury repair.

Anterior cruciate ligament (ACL) reconstruction provides an illustrative and well-characterized example of the importance of bone-tendon healing, as there are more than 239,000 cruciate ligament reconstructions performed annually, with a total cost of $3.5 billion. ACL reconstruction surgery generally involves 4 steps: 1) removal of the damaged ligament; 2) drilling of tunnels through the tibia and the femur for graft positioning; 3) placement of a hamstring tendon or patellar tendon graft into these bone tunnels using a suture as a guide; and 4) fixation of the graft with interference screws, which minimize graft motion in the femoral and tibial tunnels.

Although widely successful in enhancing knee stability, the process of cruciate ligament reconstruction is plagued by significant limitations. The first is tunnel widening. Without screw fixation 75% of patients have at least 60% widening of their femoral tunnels 30 months after surgery, and a recent study has shown that even with screw fixation the femoral and tibial tunnel areas increase by 102% and 85% twelve months after surgery. This tunnel widening is indicative of bone resorption instead of the desired tendon-bone healing, and it creates significant reconstructive challenges in the 5-10% of cases that require revision surgery. A second limitation in ACL reconstruction is the extensive amount of time required for full patient recovery, which is typically a 6 month timeframe. Taken together, these limitations cause a significant increase in patient morbidity and loss of physical activity, and these issues are typical in other clinical scenarios that require bone-tendon healing.

It has recently been demonstrated that soluble growth factors may play a role during the various stages of bone tendon healing, including the inflammatory phase, the proliferation phase, and the remodeling phase (Murphy, et al., "Healing of Bone and Connective Tissues," in *Encyclopedia of Biomaterials and Biomedical Engineering*, Wnek, G. B., ed., Informa Healthcare, 2006). For instance, a recent study indicated that the growth factors FGF-2, BMP-2, and VEGF are each upregulated during various stages of healing after ACL reconstruction surgery, and that these proteins contribute to functional bone-tendon integration (Kohno, et al., "Immunohistochemical demonstration of growth factors at the tendon-bone interface in anterior cruciate ligament reconstruction using a rabbit model," *J. Orthop. Sci.*, 2007, Vol. 12(1) p. 67-73). It has also been shown that BMP-2 delivery from a collagen sponge can promote rapid bone formation in a tibial tunnel in a canine model (Rodeo, et al., "Use of recombinant human bone morphogenetic protein-2 to enhance tendon healing in a bone tunnel," *Am. J. Sports Med.*, 1999, Vol. 27 (4), p. 476-88), and that tendon grafts soaked in a VEGF solution prior to implantation promote enhanced blood vessel growth into the bone tunnel, thereby increasing graft viability (Yoshikawa, et al., "Effects of local administration of vascular endothelial growth factor on mechanical characteristics of the semitendinosus tendon graft after anterior cruciate ligament reconstruction in sheep," *Am. J. Sports Med.*, 2006, Vol. 34(12), p. 1918-25). Other proteins, including FGF-2 and $\alpha$2-macroblobulin, have also shown promise as therapeutic agents to improve ACL reconstruction outcomes.

In view of the prevalence of growth factor signaling during orthopedic tissue healing, including bone-tending healing, strategies have been developed to deliver growth factors to skeletal tissues. Traditional "sustained" growth factor delivery approaches have focused on embedding proteins in plastic microspheres (e.g., poly(lactide-co-glycolide) microspheres) or suspending proteins in hydrogels (e.g., type I collagen gels). The advent of these technologies has had a revolutionary effect on medicine, and the worldwide market for drug delivery technology exceeds $100 billion. However, although these approaches have been useful in a wide variety of biomedical applications, their application to functional bone and tendon healing is pragmatically limited. Plastic microspheres do not represent a stand alone device for tissue ingrowth and are difficult to process into structural orthopedic devices while retaining protein biological activity. Hydrogels are also non-ideal carriers, as growth factors typically transport out of the hydrogel rapidly, resulting in limited, short-term delivery.

Recent approaches have also been developed that allow for longer term growth factor release, e.g., up to several months, within a biodegradable polymer "scaffold" that can support tissue ingrowth, including porous plastic scaffolds and chemically modified hydrogels. Although these previous growth factor delivery approaches have been successful in actively influencing bone regeneration within scaffold materials, pragmatic challenges limit the implementation of growth factor delivery strategies in clinical orthopedics. First, current growth factor delivery platforms release a substantial amount of protein in the first 48 hours of use, a phenomenon known as "burst" release. This rapid "burst" may be particularly problematic in orthopedic surgery applications, in which an acute inflammatory response in the first 3-5 days after surgery floods the local environment with blood-born growth factors that may mask the effects of the protein being delivered. Second, materials that serve as carriers for delivery of bone growth factors are typically unsuitable for clinical orthopedic applications due to their inappropriate geometry and poor bulk mechanical properties.

Bioresorbable devices constitute a significant portion of the orthopedic industry ($100.5 million total market size) and this market is expected to grow dramatically for the foreseeable future. In the cruciate ligament fixation market bioresorbable devices had a 23% market penetration in 2002 ($14.1 million total market), and this penetration is expected to increase substantially in the next 5 years. The most common class of bioresorbable polymer used clinically are the poly($\alpha$-hydroxy esters) which include poly(L-lactic acid) (PLLA), poly(lactide-co-glycolide) (PLG), poly(dioxanone) (PDS), and poly($\epsilon$-caprolactone) (PCL). These polymers are used as nails, pins, anchors, screws, plates, sutures, and scaffolds for a variety of orthopedic applications. Sutures are particularly ubiquitous, and they are a key component of virtually all bone-tendon healing applications in orthopedics. In each case, the unique goal of bioresorbable devices is to serve as temporary fixation devices, with the intent that after tissue healing the host tissues will assume this function. Therefore, proper function of these devices requires new tissue formation in concert with device resorption. However, typical bioresorbable devices do not actively promote new tissue formation, and the processing conditions used to generate these devices typically employ high temperatures and/or organic solvents that preclude incorporation of biologically active proteins (e.g., growth factors) capable of inducing new tissue growth. Therefore, there is a need for new approaches that allow for controlled protein delivery from bioresorbable devices, such as sutures, commonly used in clinical applications.

It has now been discovered that limitations associated with growth factor delivery during orthopedic tissue healing can be addressed by synthesizing a mineral layer, such as a hydroxyapatite (HAP) layer, on standard biodegradable or bioresorbable orthopedic devices, and engineering these layers to deliver growth factors or other biological substances in a spatially and temporally controlled manner.

SUMMARY OF THE DISCLOSURE

The present disclosure generally relates to biodegradable and bioresorbable materials having a mineral layer on the surface of the material. More particularly, the disclosure relates to biodegradable and bioresorbable orthopedic devices having a degradable mineral layer on the surface thereof that can be used as a delivery vehicle for biological substances. Also provided are various methods of using the mineralized devices in tissue regeneration, including bone tissue engineering, and methods for producing the mineralized devices.

Accordingly, in one embodiment, the present disclosure is directed to a biologically active suture comprising: a suture material comprising one or more filaments; at least one degradable mineral layer associated with a surface of the suture material; and at least one biological substance associated with the degradable mineral layer.

In another embodiment, the present disclosure is directed to a biologically active material for use in tissue regeneration or repair comprising: a bioresorbable material; at least one degradable mineral layer associated with a surface of the bioresorbable material; and at least one biological substance incorporated into the degradable mineral layer.

In yet another embodiment, the present disclosure is directed to a method for preparing a biologically active material for use in tissue regeneration. The method comprises: functionalizing at least one surface of a bioresorbable material to expose carboxylate anions on the surface; contacting the functionalized surface with an amount of a mineral-containing solution effective to form a degradable mineral layer on the functionalized surface; and exposing at least a portion of the degradable mineral layer to at least one biological substance until the at least one biological substance associates with the degradable mineral layer.

In yet another embodiment, the present disclosure is directed to a method for regenerating biological tissue. The method comprises: contacting the tissue with a biologically active material, the biologically active material comprising a bioresorbable material, at least one degradable mineral layer associated with a surface of the bioresorbable material, and at least one biological substance incorporated into the degradable mineral layer; and releasing the at least one biological substance from the at least one degradable mineral layer.

In yet another embodiment, the present disclosure is directed to a method for controlling the release of a biological substance from a biologically active material. The method comprises: preparing a biologically active material, the biologically active material comprising a bioresorbable material, at least one degradable mineral layer associated with a surface of the bioresorbable material; and at least one biological substance associated with the at least one degradable mineral layer; spatially controlling release of the at least one biological substance from the at least one degradable mineral layer by associating the at least one biological substance with the at least one degradable mineral layer in a pattern; and temporally controlling release of the at least one biological substance from the at least one degradable mineral layer by adjusting a characteristic of the at least one degradable mineral layer, wherein the characteristic of the at least one degradable mineral layer is selected from the group consisting of thickness, density, composition, morphology, and combinations thereof.

BRIEF DESCRIPTION OF THE DRAWINGS

FIG. 3C scale bar: 5 µm), as discussed in Example 2.

FIG. 4A plots the FT-IR spectra for lysozyme (lysozyme spectra designated "(i)"), hydroxyapatite present on the suture (hydroxyapatite spectrum designated "(ii)"), and the lysozyme-incorporated hydroxyapatite layer produced after incubation of the mineralized suture in the lysozyme solution (lysozyme-incorporated hydroxyapatite designated "(iii)").

FIG. 9 shows fluorescence micrographs taken from a single suture sequentially dipped into fluorescein-labeled BSA and rhodamine-conjugated lysozyme, as discussed in Example 7.

DETAILED DESCRIPTION OF THE DISCLOSURE

Figure 1A:
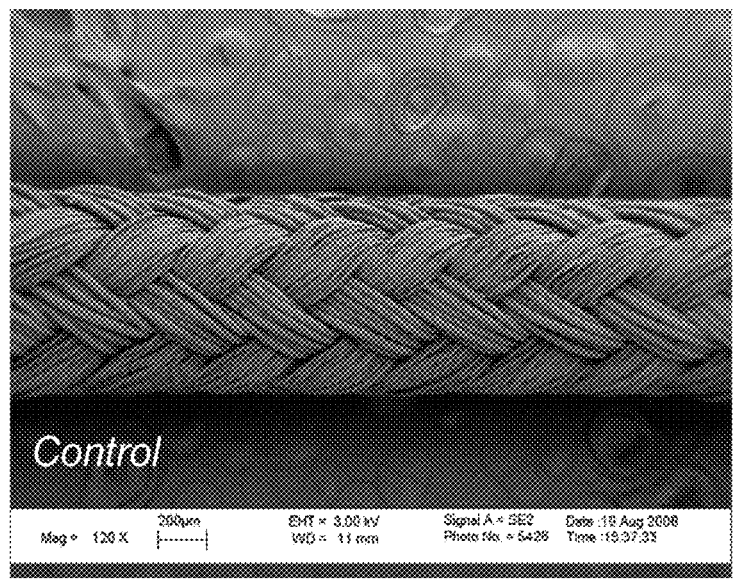
FIG. 1 depicts a 120× magnification of an untreated ORTHOCORD™ suture (FIG. 1A), an ORTHOCORD™ suture treated with 0.1 N NaOH solution for 5 minutes (FIG. 1B), an ORTHOCORD™ suture treated with 0.1 N NaOH solution for 30 minutes (FIG. 1C), and an ORTHOCORD™ suture treated with 0.1 N NaOH solution for 60 minutes (FIG. 1D), as discussed in Example 1.
Figure 1B:
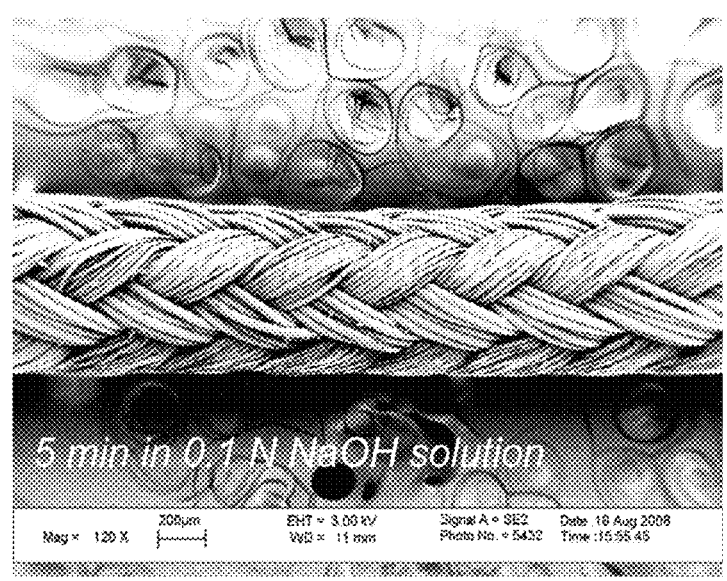
Figure 1C:
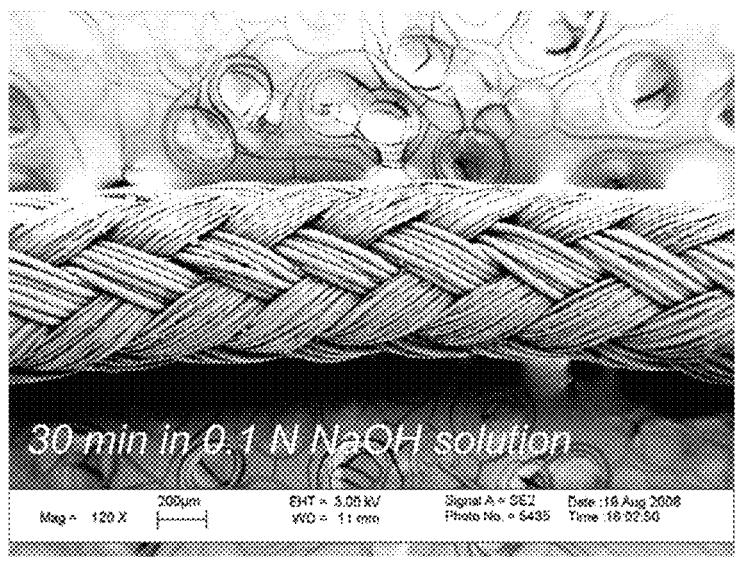

The present disclosure generally relates to biodegradable and bioresorbable materials having a mineral layer on the surface of the material. More particularly, the disclosure relates to biodegradable and bioresorbable orthopedic devices having a degradable mineral layer on the surface of the device that can be used as a delivery vehicle for biological substances. Also provided are various methods of using the mineralized devices in tissue regeneration, including bone tissue engineering, and methods for producing the mineralized devices.

Devices such as tacks, screws, anchors, plates, pins, nails, sutures, and the like, are ubiquitous and invaluable tools in surgery, and particularly in orthopedic surgery, as they enable physical linkage of distinct portions of tissues to promote healing. Although the mechanical properties and biocompatibility of such devices have been widely studied, the potential use of these devices as platforms to deliver biological substances has received little attention. However, the proximity of such devices to healing tissues coupled with their widespread use in the majority of surgical procedures suggests that they could be an ideal vehicle to promote tissue healing. This sort of vehicle could be particularly applicable to tissue regeneration, which is often limited by an inability to efficiently deliver biologically active substances.

It has now been discovered that commonly used surgical devices such as tacks, screws, anchors, plates, pins, nails, sutures, and the like, may be adapted for use as a vehicle for delivering biological substances to healing tissue. These devices are particularly suitable for use in the repair of avascular orthopedic tissue, such as the avascular portion of the meniscus of the knee, the rotator cuff, cruciate ligaments, the hand flexor tendon, and the Achilles tendon.

The devices and methods of the present disclosure thus provide a delivery system which effectively incorporates and subsequently releases biological substances from commonly used surgical devices in a controlled manner. Advantageously, the devices and methods of the present disclosure achieve this effective incorporation and release of biological substances while having minimal to no effect on the inherent mechanical properties of the devices.

Specifically, the present disclosure uses a process that mimics mineral growth in biological systems to form a degradable mineral layer on the surface of a bioresorbable material, such as a bioresorbable orthopedic device. Natural biomineralization processes typically occur at sites characterized by a high density of negatively charged peptide residues, which are thought to attract calcium-rich mineral nuclei and initiate mineral growth. The present disclosure uses a bioresorbable material as a template to induce growth of a mineral layer on the surface of the bioresorbable material. Specifically, the surface of the bioresorbable material is functionalized to expose carboxylate anions on the surface of the material. The carboxylate anions serve as nucleation sites for the formation of a degradable calcium and phosphate-rich mineral layer on the surface of the bioresorbable material. The degradable mineral layer may then be exposed to at least one biological substance, such that the biological substance is associated with and/or incorporated into the degradable mineral layer. The resulting biologically active material may be used as a vehicle for promoting tissue healing and regeneration.

Advantageously, the formation of the degradable mineral layer and the association of the biological substances with the degradable mineral layer may be adjusted to provide for both spatial and temporal control over the release of the biological substance from the degradable mineral layer. In particular, it has been discovered that by adjusting one or more characteristic of the degradable mineral layer, such as the thickness of the degradable mineral layer, the density of the degradable mineral layer, the number of degradable mineral layers, the type of mineral in the degradable mineral layer, the carbonate substitution for phosphate in the degradable mineral layer, and the like, or some combination thereof, the rate of release of the biological substance from the degradable mineral layer can be controlled. Additionally, the release of the biological substances from the degradable mineral layer may be spatially controlled by specifically controlling the location on the degradable mineral layer at which the biological substance is located. Specifically, the biological substance may be incorporated into or onto the degradable mineral layer in a pattern.

Thus, in one aspect, the present disclosure is directed to a biologically active material for use in tissue regeneration or repair. The biologically active material comprises a bioresorbable material; at least one degradable mineral layer associated with a surface of the bioresorbable material; and at least one biological substance incorporated into the degradable mineral layer. In one particular embodiment, a biologically active suture is provided. The biologically active suture may comprise a suture material comprising one or more filaments; at least one degradable mineral layer associated with a surface of the suture material; and at least one biological substance associated with the degradable mineral layer. Methods for preparing the biologically active materials, as well as methods for regenerating biological tissue and methods for controlling the release of a biological substance from the biologically active materials are also provided.

As noted above, the biologically active materials of the present disclosure may have a variety of applications. In one particular embodiment, the biologically active materials are used in the field of orthopedics. Examples of suitable biologically active materials may thus include polymeric orthopedic devices, as well as polymeric particulates such as microspheres, injectable delivery carriers, stents, catheters, sutures, and combinations thereof. Non-limiting examples of suitable polymeric orthopedic devices include tacks, screws, anchors, plates, pins, nails, sutures, joint replacements, prostheses, and combinations thereof.

In one particular embodiment, the biologically active material is a suture. The suture may be formed of any suitable material, for example one or more filaments. In one particular embodiment, the suture is a braided suture. Advantageously, the suture may comprise a bioresorbable suture material. Examples of suitable sutures are also commercially available and include the ORTHOCORD™ Orthopaedic Suture (DePuy Mitek, Raynham, Mass.), POLYSORB™, DEXON™ II, DEXON™ S, BIOSYN™, MAXON™, MAXON™ CV (all available from Covidien, Mansfield, Mass.), VICRYL™, PDS™ II, MONOCRYL™ (all available from Ethicon, Somerville, N.J.).

The biologically active materials of the present disclosure may be formed of a variety of materials. Examples of suitable materials include biodegradable, non-biodegradable, bioresorbable, or non-bioresorbable materials. Examples of non-biodegradable, non-bioresorbable materials include poly(methyl methacrylate), poly(2-hydroxyethyl methacrylate), poly(ethylene terephthalate, polyethylene, poly(ether sulfone), polyamide, polytetrafluoroethylene, polysaccharide, and combinations thereof.

In one particular embodiment, the biologically active material comprises a biodegradable or bioresorbable material. The terms "biodegradable" and "bioresorbable," used interchangeably herein, refer to any material that can be broken down under physiological conditions. Non-limiting examples of suitable bioresorbable materials include synthetic poly(α-hydroxy esters), natural alginates, poly(ester urethanes), and combinations thereof. Examples of suitable synthetic poly(α-hydroxy esters) include polyglycolide (PGA), poly(glycolide-co-lactide) (PLGA), polycaprolactone (PCL), polydioxanone (PDS), polycarbonates, polyamides, polylactones, polysaccharides, poly(ethylene terephthalate), copolymers of poly(α-hydroxy esters), and combinations thereof.

As noted above, the biologically active materials of the instant disclosure comprise at least one degradable mineral layer associated with a surface of the bioresorbable material. The degradable mineral layer or layers are formed of bone-like minerals. In particular, materials suitable for forming the degradable mineral layer may include bone mineral ions, such as, but not limited to, calcium, phosphate, and carbonate, as well as combinations of bone mineral ions, such as calcium phosphates. Non-limiting examples of suitable minerals that can form the degradable mineral layer include hydroxyapatite, α-tricalcium phosphate, β-tricalcium phosphate, amorphous calcium phosphate, dicalcium phosphate, octacalcium phosphate, calcium carbonate, calcium sulfate, and combinations thereof. Preferably, the mineral is hydroxyapatite.

Typically, the degradable mineral layer will comprise calcium and phosphate in a ratio of from about 1:1.0 to about 1:2.0, and more typically in a ratio of from about 1:1.5 to about 1:1.8. It should be understood that the ratio will vary depending on the type of mineral used in the degradable mineral layer.

As noted above, the process used to form the degradable mineral layer or layers mimics natural mineral growth in biological systems. Natural biomineralization processes typically occur at sites characterized by a high density of negatively charged peptide residues, which are thought to attract calcium-rich mineral nuclei and initiate mineral growth. The present disclosure uses the bioresorbable material as a template to induce growth of the degradable mineral layer on the surface of the bioresorbable material. Specifically, at least one surface of the bioresorbable material is functionalized to expose carboxylate anions on the surface of the bioresorbable material. The carboxylate anions serve as nucleation sites for the formation of the degradable mineral layer on the surface of the bioresorbable material.

The surface of the bioresorbable material may be functionalized using any suitable technique. In one embodiment, the surface of the bioresorbable material is chemically functionalized, for example, by hydrolysis of the surface. Specifically, the bioresorbable material is exposed to a hydrolysis solution, for example, a solution of sodium hydroxide. In another embodiment, the bioresorbable material is functionalized using an acidic solution such as hydrochloride or a basic solution such as potassium hydroxide. In yet another embodiment, the bioresorbable material is functionalized using any enzyme known to be suitable for hydrolysis.

The degree of surface hydrolysis of the bioresorbable material will affect the properties of the degradable mineral layer. Specifically, the degree of hydrolysis may affect the morphology and crystal size of the degradable mineral layer by affecting the interaction between the polymer surface and clusters of mineral ions in solution (see Murphy, et al., J. Am. Chem. Soc., 2002, Vol. 124, p. 1910-1917).

Depending on the type of solution and the concentration of the hydrolyzing agent in solution, the bioresorbable material may be exposed to the hydrolysis solution for a period of from about 0 to about 60 minutes. For example, when the solution is a 0.5 N sodium hydroxide solution, the bioresorbable material is typically exposed for a period of from about 30 minutes to about 60 minutes. In one embodiment, the bioresorbable material is exposed to the hydrolysis solution for about 1 hour. In some embodiments, such as when the solution is water of a physiologic buffer, however, mineralization of the bioresorbable material occurs without the hydrolysis step. It should be understood that the hydrolysis time may be adjusted depending on the concentration of the hydrolysis solution.

Following functionalization, the bioresorbable material may optionally be rinsed, for example with water, to remove excess hydrolysis solution.

In other embodiments, the surface of the bioresorbable material may be functionalized by photolysis or electrolysis, such as is described in U.S. Pat. No. 6,767,928, which is hereby incorporated by reference to the extent it is consistent herewith.

Following functionalization, the functionalized surface of the bioresorbable material may be contacted with an amount of a mineral-containing solution effective to form the degradable mineral layer on the functionalized surface. The mineral-containing solution comprises materials suitable for forming the degradable mineral layer, including bone mineral ions such as calcium, phosphate, and carbonate, as well as combinations of bone mineral ions, such as calcium phosphates.

In one particular embodiment, the mineral-containing solution is a simulated body fluid (SBF) or a modified simulated body fluid (mSBF), which has 2-fold higher concentrations of calcium chloride and potassium phosphate as compared to SBF. One example of a suitable mSBF is set forth in Example 1, and comprises 141 mM NaCl, 4 mM KCl, 0.5 mM $MgSO_4$, 1.0 mM $MgCL_2$, 4.2 mM $NaHCO_3$, 5 mM $CaCl_2$, 1.0 mM $KH_2PO_4$, and 20 mM Tris base.

The functionalized surface of the bioresorbable material may be contacted with the mineral-containing solution, for example, by incubating the bioresorbable material in the mineral-containing solution for at least about 3 days, more typically for from about 3 to about 20 days, and more typically for about 7 days. In one particular embodiment, the bioresorbable material is incubated in the mineral-containing solution for about 7 days. Preferably, the mineral-containing solution is refreshed (i.e., replaced) after each day of incubation.

Typically, the incubation will occur at a physiological temperature and pH. For instance, the bioresorbable material may be incubated in the mineral-containing solution at a temperature of from about 15° C. to about 40° C., and at a pH of from about 5.0 to about 8.0. In one particular embodiment, the bioresorbable material is incubated in the mineral-containing solution at a temperature of about 37° C. and a pH of about 6.8.

It should be understood that the conditions under which incubation occurs will affect the type of mineral layer formed. In general, an increase in pH favors hydroxyapatite growth, while a decrease in pH favors octacalcium phosphate mineral growth. For example, conditions favorable for hydroxyapatite formation include a pH of from about 5.0 to about 8.0.

Following incubation in the mineral-containing solution, the bioresorbable material may optionally be rinsed to remove excess solution. The bioresorbable material may then optionally be freeze dried following rinsing. The bioresorbable material may be freeze dried for a period of at least about 12 hours. In one embodiment, the bioresorbable material is freeze dried for about 1 day.

The resulting bioresorbable material comprises a degradable mineral layer associated with a surface of the bioresorbable material. The degradable mineral layer is porous and displays a plate-like nanostructure, similar to the structure and composition found in vertebrate bone mineral.

As discussed herein, the thickness of the degradable mineral layer may be adjusted, depending on the desired release profile of the biological substance from the degradable mineral layer. More particularly, the thickness of the layer is typically controlled by the incubation time as described above. Generally, thicker layers allow for longer sustained release of the biological substance than do thinner layers.

The density of the degradable mineral layer may likewise be adjusted depending on the desired rate of release of the biological substance from the degradable mineral layer. Generally, the denser the layer, the lesser surface area is available for biological substance binding, allowing for less incorporation and less release of the biological substance. The density may be adjusted depending on the selection of the incubating media. For example, using higher calcium and phosphate levels will generate less dense layers.

As noted above, the biologically active material further comprises at least one biological substance associated with and/or incorporated into the degradable mineral layer. A wide variety of biological substances may be used. Biological substances include those substances which can act on cells and/or biological tissues, for example, to promote healing and/or tissue regeneration.

Examples of suitable biological substances include nucleic acids including DNA molecules, RNA molecules, and antisense nucleic acids, ribozymes, plasmids, expression vectors, viral vectors, recombinant viruses, marker proteins, transcription or elongation factors, cell cycle control proteins, kinases, phosphatases, DNA repair proteins, oncogenes, tumor suppressors, angiogenic proteins, anti-angiogenic proteins, cell surface receptors, accessory signaling molecules, transport proteins, enzymes, anti-bacterial agents, anti-viral agents, antigens, immunogens, apoptosis-inducing agents, anti-apoptosis agents, cytotoxins, and combinations thereof.

The biological substances may further include hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides such as growth hormone, parathyroid hormone (PTH), bone morphogenetic protein (BMP)-2, BMP-7, transforming growth factor-α (TGF-α), TGF-β1, TGF-β2, fibroblast growth factor-2 (FGF-2), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin, vascular endothelial growth factor (VEGF), and combinations thereof. In one particular embodiment, the biological substance is selected from the group consisting of FGF-2, BMP-2, BMP-7, VEGF, PDGF, TGF-β1, and combinations thereof.

In some embodiments, the biological substance is selected from the group consisting of cells, cytokines, growth factors, hormones, nucleic acids, enzymes, and combinations thereof. In one particular embodiment, the biological substance is a cytokine selected from the group consisting of interleukin-1, ineterleukin-6, tumor necrosis factor-α, and combinations thereof.

In another embodiment, the biological substance is selected form the group consisting of lysozyme, bovine serum albumin, and combinations thereof.

Combinations of any of the aforementioned biological substances may also be used.

As discussed above, the biological substance is associated with the degradable mineral layer. For instance, the biological substance may be incorporated into the degradable mineral layer, e.g., located in the interior of the mineral layer, by associating with pores in the mineral layer. Alternately or in addition, the biological substances may be bound to the surface of the degradable mineral layer through electrostatic interaction. Furthermore, in some embodiments, the biological substances may be bound to the interior surface of the pores. When multiple layers are used, the biological substances may be sandwiched between the mineral layers.

In some embodiments, the biological substance is incorporated into the mineral layer using co-precipitation. Specifically, the biological substance may be incorporated into the SBF or mSBF and incorporated into the mineral layer simultaneously with the formulation of the mineral layer.

The biological substance is associated with and/or incorporating into the degradable mineral layer by exposing the degradable mineral layer or a portion thereof to the biological substance. In one embodiment, the degradable mineral layer is exposed to the biological substrate by incubating the bioresorbable material comprising the degradable mineral layer in a solution comprising the biological substrate. The solution will typically comprise the biological substrate at a concentration of from about 10 μg/mL to about 1000 μg/mL.

The bioresorbable material may be incubated in the solution for from about 5 minutes to about 12 hours, and more typically for from about 10 minutes to about 10 hours, and even more typically for about 4 hours.

Advantageously, the bioresorbable material is incubated in the solution at physiological temperature and pH. For instance, the bioresorbable material may be incubated in the solution at a temperature of from about 15° C. to about 40° C., and at a pH of from about 5.0 to about 9.0, or from about 6.5 to about 8.0. In one embodiment, the bioresorbable material may be incubated in the solution at a temperature of about 37° C. and a pH of about 7.4.

In another embodiment, the degradable mineral layer or portion thereof is exposed to the biological substance by applying the solution comprising the biological substance to the degradable mineral layer or a portion thereof. The biological substance may be applied to the degradable mineral layer by any suitable technique including, for example, pipetting the solution comprising the biological substance(s) onto the desired portion of the degradable mineral layer, brushing the solution onto the desired portion of the degradable mineral layer, stamping the solution onto the degradable mineral layer, immersing the degradable mineral layer into the solution (i.e., dip-coating), or combinations of these techniques.

The amount of the biological substance incorporated into and/or associated with the degradable mineral layer will depend on the concentration of the biological substance in the solution, the type of biological substance to be incorporated, the type of mineral layer used, the morphology of the mineral layer used, and the ionic condition of the solution, and may be adjusted depending on the desired release profile for the biological substance.

As discussed herein, the biologically active materials of the present disclosure may comprise more than one biological substance. It is to be understood that the type and amount of biological substances associated with the degradable mineral layer will vary depending on the desired application of the biologically active material.

In one embodiment, the biologically active material comprises at least two biological substances. The biological substances may be associated with the same region of the degradable mineral layer and/or may be associated with different regions of the degradable mineral layer.

In embodiments where the biological substances are associated with the same region of the degradable mineral layer, the biologically active material may be prepared by incubating the bioresorbable material comprising the degradable mineral layer in a first solution comprising the first biological substance and subsequently incubating the bioresorbable material in a second solution comprising the second biological substance, under the conditions described above. Alternately, the bioresorbable material may be incubated in a single solution comprising both the first and second (and/or any additional) biological substances, under the conditions described above.

Biologically active materials comprising two or more biological substances associated with the same region of the degradable mineral layer may also be prepared by applying a first solution comprising a first biological substance to the desired region of the degradable mineral layer and subsequently applying a second solution comprising a second biological substance to an overlapping region of the degradable mineral layer, using any of the techniques described herein. Alternately, a solution comprising both the first and second (and/or any additional) biological substances may be applied to the desired regions of the degradable mineral layer.

As discussed herein, the release of the biological substances from the degradable mineral layer may be spatially controlled by specifically controlling the location on the degradable mineral layer at which the biological substance is located. This may be achieved by incorporating the biological substance(s) into or onto the degradable mineral layer in a pattern. The patterns may be formed by, for example, applying one or more biological substance to the degradable mineral layer by pipetting the solution comprising the biological substance(s) onto the desired portion of the degradable mineral layer, brushing the solution onto the desired portion of the degradable mineral layer, and/or stamping the solution onto the degradable mineral layer, as described above. Combinations of these techniques may also be used.

The pattern may vary depending on the desired use of the biologically active material. In one embodiment, the pattern comprises alternating regions of different biological substances. In another embodiment, a first and a second biological substance may be applied to the degradable mineral layer such that the first biological substance is located on a first side of the biologically active material and the second biological substance is located on a second side of the biologically active material. Other suitable patterns may also be used.

As discussed herein, the release of the biological substance(s) from the degradable mineral layer may also be temporally controlled by adjusting one or more characteristics of the degradable mineral layer. A variety of factors may affect the rate at which the biological substance(s) is released from the degradable mineral layer including, for example, the thickness of the degradable mineral layer, the density of the degradable mineral layer, the composition of the degradable mineral layer, the degree of hydrolysis of the bioresorbable material prior to formation of the mineral layer, the number of degradable mineral layers, the pH of the fluid in which the biologically active material is located, or combinations thereof. Thus, depending on the application, one or more of these parameters may be adjusted to achieve the desired release profile.

For instance, the type of mineral in the mineral layer may affect the rate at which the mineral layer degrades and subsequently releases the biological substance(s). Different minerals have different rates of degradation. In particular, the rate of dissolution increases with the decreasing calcium to phosphorus ratio. For example, the order of solubility for certain minerals is amorphous calcium phosphate>dicalcium phosphate>α-tricalcium phosphate>β-tricalcium phosphate>hydroxyapatite.

In some aspects, the biologically active material comprises two or more degradable mineral layers. In such a multi-layered embodiment, a second (or multiple) additional degradable mineral layer may be formed on the surface of the first formed degradable mineral layer. The second (or multiple) additional degradable mineral layer may be formed using any of the techniques described herein. For instance, the bioresorbable material comprising the first degradable mineral layer may be contacted with an amount of the mineral-containing solution effective to form the second degradable mineral layer on the surface of the first degradable mineral layer. The techniques described herein may be repeated as many times as needed to form the desired number of degradable mineral layers.

It should be understood that any of the second (or multiple) additional degradable mineral layer(s) may also be associated with one or more biological substance(s) by exposing the second (or multiple) additional degradable mineral layer(s) or a portion thereof to the biological substance(s), using any of the techniques described herein. The biological substance(s) may be the same biological substance and/or may be a different biological substance(s) as that associated with the first degradable mineral layer.

In one aspect, the biologically active material may include one or more additional degradable mineral layer that is not associated with a biological substance. Such degradable mineral layers may be used to temporally control the release of biological substance(s) from other degradable mineral layers. Specifically, a degradable mineral layer that is not associated with a biological substance may be used to delay the release of biological substance(s) from other degradable mineral layer(s).

Since the biological substance is released upon degradation of the degradable mineral layer, the amount of biological substance released can be measured by determining the rate of mineral layer degradation. This may be expressed, for example, in terms of the amount of calcium released from the degradable mineral layer.

In one embodiment, the biological substance may be continuously released from the degradable mineral layer. For instance, the biological substance(s) may be released from the degradable mineral layer at a continuous rate over a period of at least about 20 days.

Since the methods are performed and the biologically active materials are prepared under physiological conditions, a high percentage of the biological substance that is released from the degradable mineral layer is biologically active upon release. Advantageously, at least about 90% of the biological substance is active after release from the degradable mineral layer.

As noted above, the biologically active materials of the present disclosure may be used as a vehicle for promoting tissue healing and regeneration. Thus in one aspect, the present disclosure further provides a method for regenerating biological tissue. Specifically, a biologically active material of the present disclosure is contacted with the target tissue. Upon release of the biological substance(s) from the degradable mineral layer(s), the biological substance(s) interact with the biological tissue, promoting tissue healing and regeneration. These methods may be used on any biological tissue, including the avascular portion of the meniscus of the knee, the rotator cuff, and cruciate ligaments, bone tissues, hand flexor tendon, Achilles tendon, and the like. The biologically active material may be surgically implanted into the tissue.

The present disclosure is further described with reference to the following illustrated Examples. Unless defined otherwise, all technical and scientific terms used herein have the same meaning as commonly illustrated by one of ordinary skill in the art of the disclosure. Although any methods and materials similar or equivalent to those described herein can be used in the practice of the disclosure, the preferred methods and materials have been described. Unless mentioned otherwise, the techniques employed or contemplated herein are standard methodologies well-known to one of ordinary skill in the art. The materials, methods and Examples are illustrative only and not limiting. All references cited herein are incorporated by reference.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this example, a hydroxyapatite mineral layer was applied to the surface of sutures.

Figure 1D:
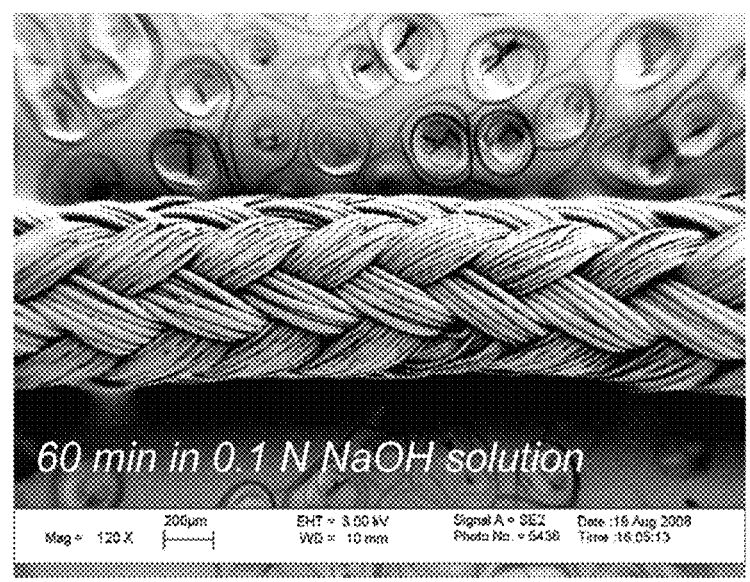
Figure 2A:
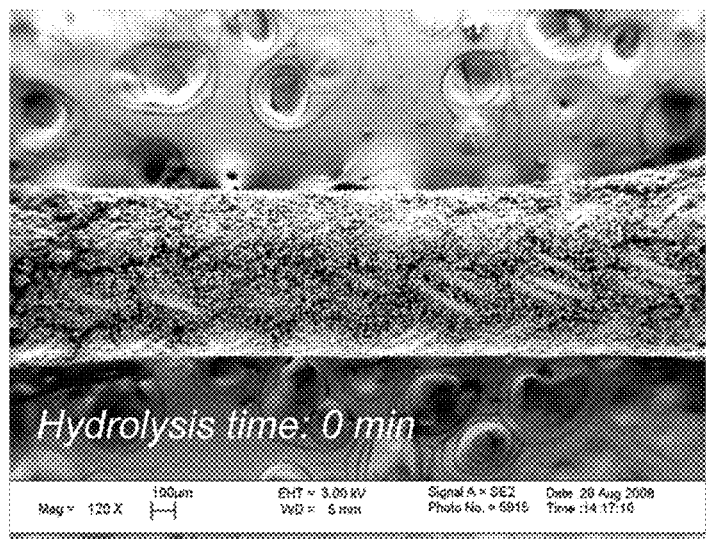
FIG. 2 depicts a 120× magnification of an untreated ORTHOCORD™ suture (FIG. 2A), an ORTHOCORD™ suture hydrolyzed for 5 minutes (FIG. 2B), an ORTHOCORD™ suture hydrolyzed for 30 minutes (FIG. 2C), and an ORTHOCORD™ suture hydrolyzed for 60 minutes (FIG. 2D) after incubation in mSBF for 7 days, as discussed in Example 1.
Figure 2B:
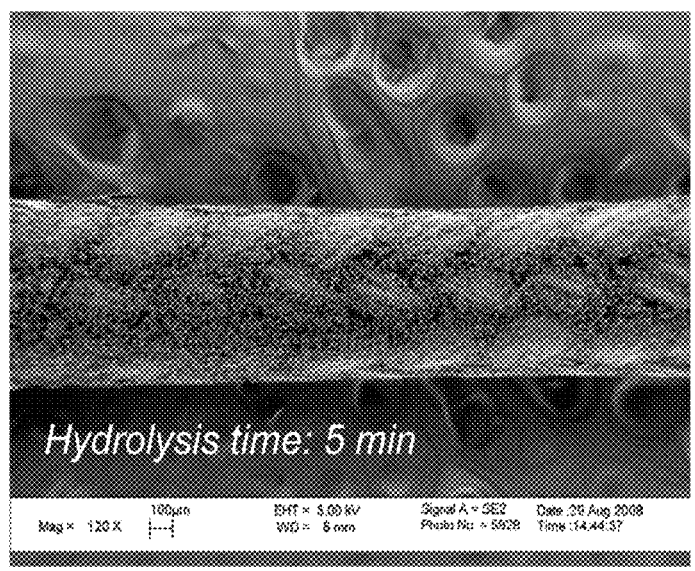
Figure 2C:
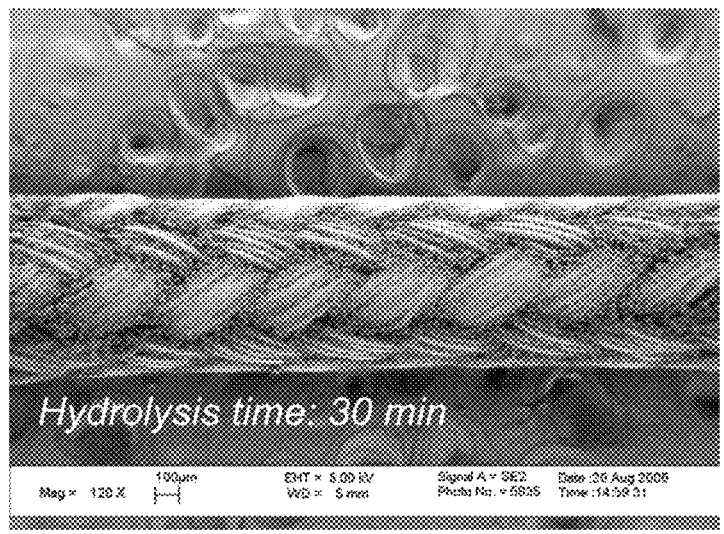
Figure 2D:
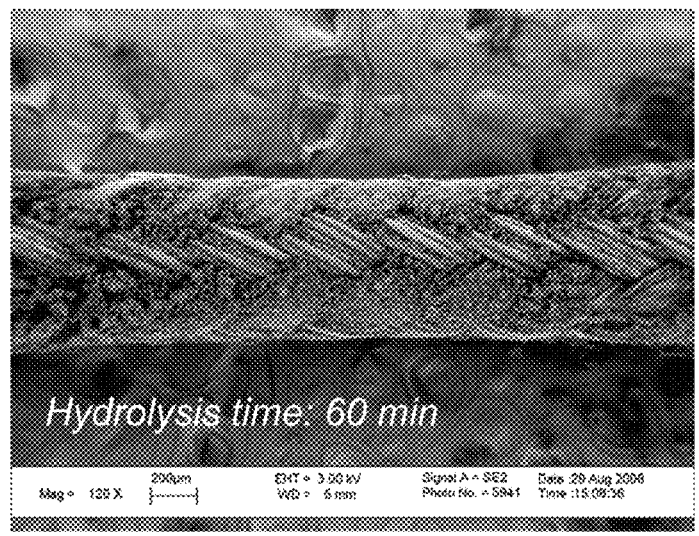

To begin, ORTHOCORD™ (USP No. 2; DePuy Mitek, Raynham, Mass.) sutures were treated with 0.1 N NaOH solution for 5 minutes, 30 minutes, or 1 hour. The resulting sutures were hydrolyzed and contained carboxylic acid groups on the suture surface. FIG. 1 depicts a 120× magnification (using LEO 1530 FE-SEM, Zeiss, Germany) of an untreated ORTHOCORD™ suture (FIG. 1A), an ORTHOCORD™ suture treated with 0.1 N NaOH solution for 5 minutes (FIG. 1B), an ORTHOCORD™ suture treated with 0.1 N NaOH solution for 30 minutes (FIG. 1C), and an ORTHOCORD™ suture treated with 0.1 N NaOH solution for 60 minutes (FIG. 1D). As can be seen from FIGS. 1A-1D, the hydrolysis procedure caused no appreciable morphological or mass change in the suture.

The hydrolyzed, carboxylic acid-rich sutures were then incubated in modified simulated body fluid (mSBF; 141 mM NaCl, 4 mM KCl, 0.5 mM MgSO$_4$, 1.0 mM MgCL$_2$, 4.2 mM NaHCO$_3$, 5 mM CaCl$_2$, 1.0 mM KH$_2$PO$_4$, 20 mM Tris base) at pH 6.8 and at 37° C. with gentle shaking for 7 days. During the 7-day mineralization, the mSBF solution was replaced daily with fresh mSBF solution.

FIG. 2 depicts a 120× magnification (using LEO 1530 FE-SEM, Zeiss, Germany) of the untreated ORTHOCORD™ suture (FIG. 2A), the ORTHOCORD™ suture hydrolyzed for 5 minutes (FIG. 2B), the ORTHOCORD™ suture hydrolyzed for 30 minutes (FIG. 2C), and the ORTHOCORD™ suture hydrolyzed for 60 minutes (FIG. 2D) after incubation in the mSBF for 7 days. Mineralization of the suture for 1 hour resulted in a suture mass gain of 55±10 µg/mm (original suture was ~280 µg/mm).

Example 2

In this example, the hydroxyapatite mineral layer applied to the sutures in Example 1 was evaluated.

The morphology and composition of the mineralized surface of sutures, prepared as described in Example 1 (60 minute hydrolysis), were characterized using LEO 1530 field-emission scanning electron microscopy (FE-SEM; Zeiss, Germany) equipped with energy dispersive spectroscopy (EDS), respectively.

Figure 3A:
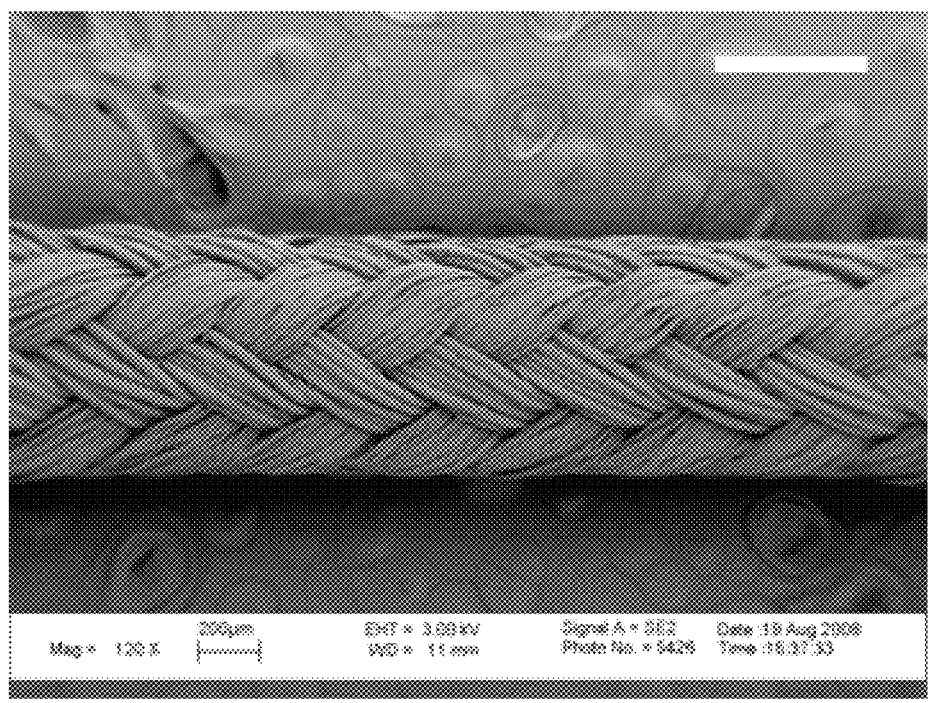
FIG. 3A shows a SEM micrograph of uncoated ORTHOCORD™ suture (scale bar: 500 µm), as discussed in Example 2.
Figure 3B:
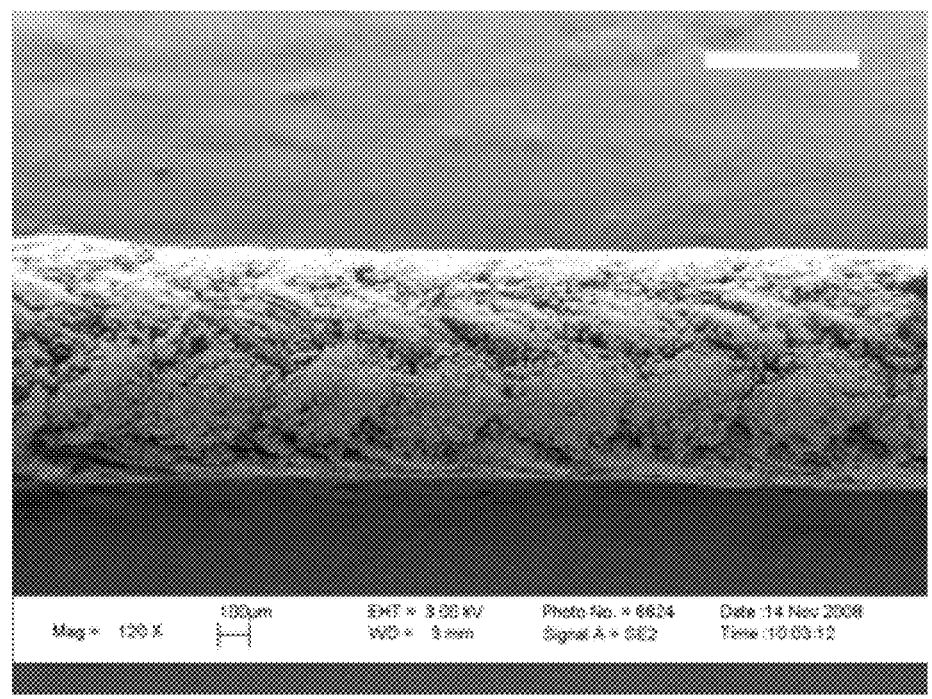
FIGS. 3B and 3C show SEM micrographs of a mineralized ORTHOCORD™ suture, prepared using the 7-day mineralization procedure described in Example 1 (FIG. 3B scale bar: 500 µm.
Figure 3C:
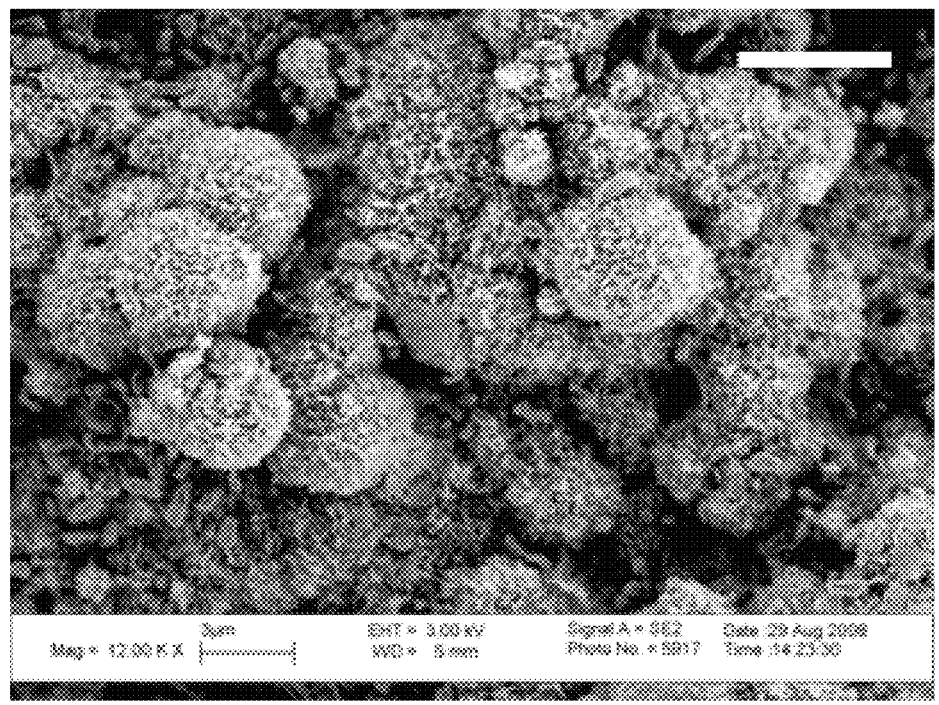

Scanning electron microscopy results are shown in FIGS. 3A-3C. FIG. 3A shows a SEM micrograph of uncoated ORTHOCORD™ suture (scale bar: 500 µm), and FIGS. 3B and 3C show SEM micrographs of a mineralized ORTHOCORD™ suture, prepared using the 7-day mineralization procedure described in Example 1 (FIG. 3B scale bar: 500 µm; FIG. 3C scale bar: 5 µm). As can be seen from FIGS. 3B and 3C, the mineral phase uniformly covers the entire surface of the suture (FIG. 3B) and has plate-like microstructure with nanoscale porosity (FIG. 3C) similar to human bone material.

Figure 3D:
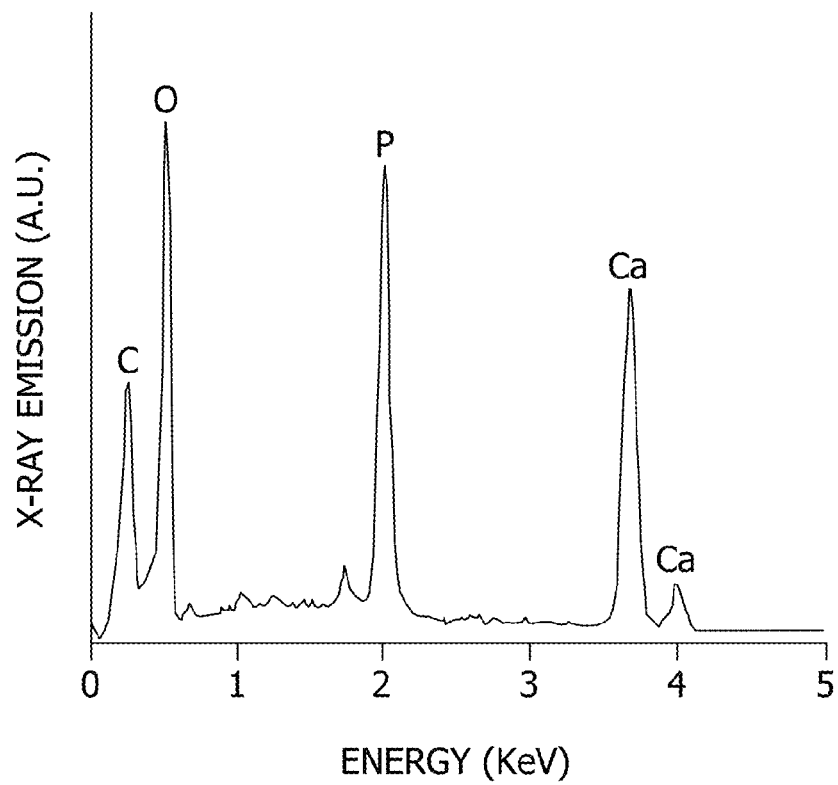
FIG. 3D is a chart showing the results of energy dispersive spectroscopy of a mineralized suture, as discussed in Example 2.

Energy dispersive spectroscopy (EDS) results are shown in FIG. 3D. As can be seen from FIG. 3D, mineralization of the suture in mSBF resulted in a compositional change of the surface of the suture to bear a significant quantity of calcium and phosphate in the ratio of calcium:phosphate of 1:1.641±0.106. This indicates growth of bone-like mineral on the surface of the suture.

Fourier transform infrared (FT-IR) spectrometry (Equinox 55 spectrometer, Bruker AXS, Germany) and X-ray diffraction (XRD) spectroscopy (Hi-Star 2-D, Bruker AXS, Germany) was also carried out on the mineralized suture of Example 1 to verify the phase of mineral coating.

Figure 3E:
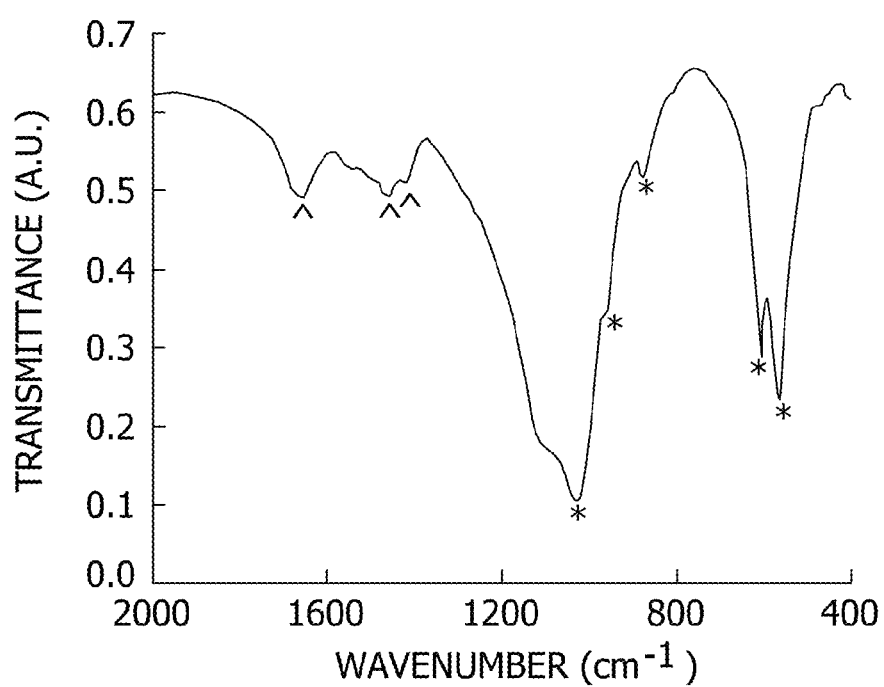
FIG. 3E is a chart showing the results of Fourier transform infrared (FT-IR) spectrometry carried out on a mineralized suture, as discussed in Example 2.

FT-IR results are shown in FIG. 3E. As can be seen from FIG. 3E, characteristic peaks associated with both apatic phosphate (denoted by "*") and carbonate substitution (denoted by "^") were detected in FT-IR spectrum, suggesting that the mineral phase created on the suture is predominantly carbonated, calcium-deficient hydroxyapatite.

Figure 3F:
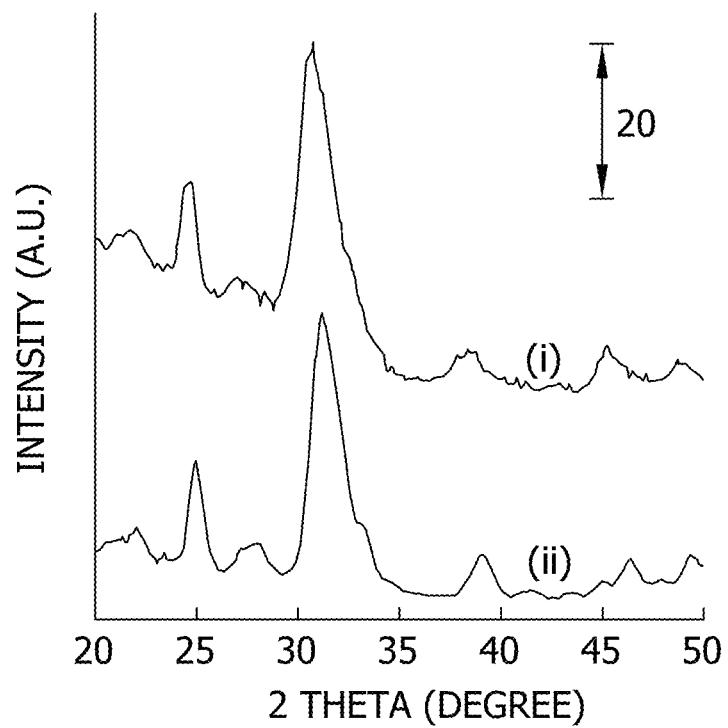
FIG. 3F is a chart showing the X-ray diffraction (XRD) pattern of the mineral phase formed on an ORTHOCORD™ suture (denoted "(i)") as compared to that of commercially available hydroxyapatite powder (denoted "(ii)"), as discussed in Example 2.

X-ray diffraction (XRD) data is shown in FIG. 3F. As can be seen from FIG. 3F, the XRD pattern of the mineral phase formed on the ORTHOCORD™ suture (denoted "(i)") is analogous to that of commercially available hydroxyapatite powder (denoted "(ii)") (commercially available from Sigma Aldrich, Catalog No. 289396, St. Louis, Mo.).

These results indicate that the mineral coating phase formed on the suture via mSBF incubation is carbonate-rich, calcium-deficient bone-like hydroxyapatite.

Example 3

In this example, the ability of a hydroxyapatite-coated suture to incorporate protein was evaluated.

To begin, a mineralized ORTHOCORD™ suture, prepared as described in Example 1 (~7 mm, 60 minute hydrolysis), was incubated for 4 hours at 37° C. in a 150 µL solution of either lysozyme (14,300 Da, isoelectric point (pI) 10.7, hydrodynamic radius ($R_H$) 1.9 nm, charge 8.5) or cytochrome c (11700 Da, pI 10.2, $R_H$ 1.8 nm, charge 9.5) in PBS (pH 7.4) to allow for incorporation of the protein molecules into the mineralized layer. The concentration of lysozyme or cytochrome c in the protein solutions varied from 100-1000 µg/mL. Specifically, protein concentrations of 100 µg/mL, 200 µg/mL, 400 µg/mL, 600 µg/mL, 800 µg/mL, and 1000 µg/mL were used.

Figure 4A:
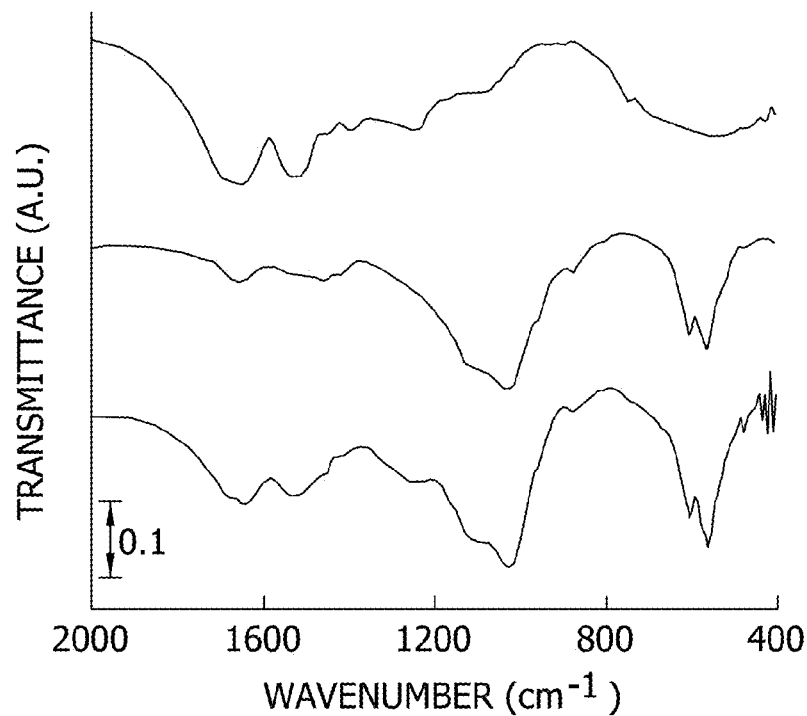
FIG. 4A is a chart showing the results of Fourier transform infrared (FT-IR) spectrometry carried out on a mineralized suture incubated in a lysozyme solution, as discussed in Example 3.
Figure 4B:
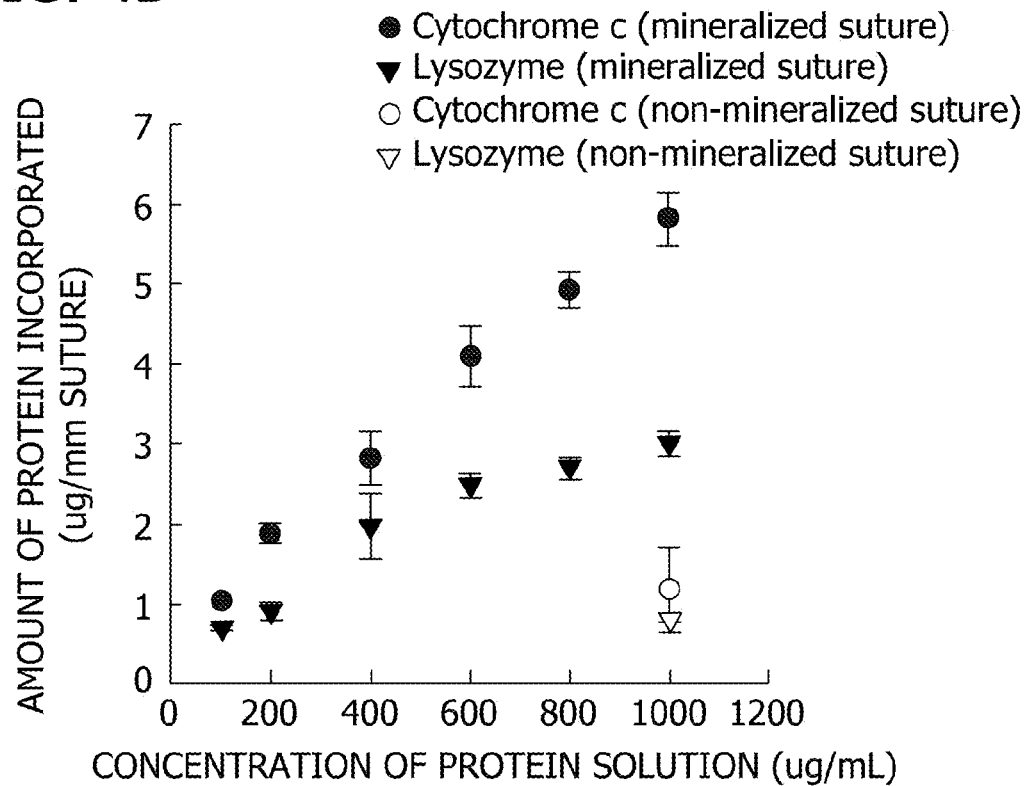
FIG. 4B is a chart showing the concentration of lysozyme (▼) and cytochrome c (•) incorporated into a mineral layer on a suture incubated in varying concentrations of lysozyme and cytochrome c, and the concentration of lysozyme (upside down open triangle) and cytochrome c (○) absorbed by a non-mineralized suture incubated in 1000 μg/mL of either lysozyme or cytochrome c, as discussed in Example 3.

Fourier transform infrared (FT-IR) spectrometry (Equinox 55 spectrometer, Bruker AXS, Germany) was carried out on the mineralized suture incubated in the lysozyme solution. The results are shown in FIG. 4A. Specifically, FIG. 4A plots the FT-IR spectra for lysozyme (lysozyme spectra designated "(i)"), hydroxyapatite present on the suture (hydroxyapatite spectrum designated "(ii)"), and the lysozyme-incorporated hydroxyapatite layer produced after incubation of the mineralized ORTHOCORD™ suture in the lysozyme solution (lysozyme-incorporated hydroxyapatite designated "(iii)"). The FT-IR spectra plotted in FIG. 4A shows clearly that amide peaks (1450~1700 cm$^{-1}$) from the lysozyme protein molecule became prominent after protein uptake. As shown in FIG. 4B, the capacity of the mineralized ORTHOCORD™ suture to bind lysozyme was found to increase proportionally with the concentration of the lysozyme solution within the experimental range (i.e., 100-1000 µg/mL).

The concentration of lysozyme and cytochrome c remaining in the incubation solution after protein binding was determined using a Micro BCA protein assay (Pierce, Rockford, Ill.). The results are shown in FIG. 4B (average of 3; standard deviation n=3). When incubated in 1000 µg/mL protein solution, the amount of lysozyme incorporated into the mineral layer on the suture (i.e., binding capacity) was 2.93±0.16 µg/mm, and the amount of cytochrome c incorporated into the mineral layer on the suture (i.e., binding capacity) was 5.77±0.32 µg/mm.

Without wishing to be bound to any particular theory, it is believed that the difference in uptake of between the cytochrome c and lysozyme is likely attributed to the surface hydrophobicity of the protein molecules. It has been shown using hydrophobic interaction chromatography that lysozyme has relatively more hydrophobic surface than cytochrome c (Min Lu, et al., "Partitioning of proteins and thylakoid membrane vesicles in aqueous two-phase systems with hydrophobically modified dextran," Journal of Chromatography A, 1994, vol. 668, pp. 215-228). Therefore, in a given condition, the hydrophobic character of the lysozyme may impose a restriction on contact between the lysozyme and the hydroxyapatite, consequently resulting in lower lysozyme binding level, as compared to cytochrome c.

In contrast to the mineralized ORTHOCORD™ sutures, non-treated ORTHOCORD™ sutures incubated in 1000 µg/mL of protein solution, as described above, absorbed only 1.12±0.51 µg/mm of cytochrome c and only 0.73±0.02 µg/mm lysozyme. These results suggest that the hydroxyapatite layer remarkably enhances protein binding through charge-charge interaction rather than nonspecific adsorption.

Example 4

In this example, the ability of a hydroxyapatite-coated suture to be used as a delivery vehicle for biological substances was evaluated. Specifically, the release kinetics of lysozyme from hydroxyapatite-coated ORTHOCORD™ sutures was determined using two distinct buffers with different pH as a release medium.

To begin, lysozyme was incorporated into mineralized sutures, prepared as described in Example 1 (60 minute hydrolysis) by incubating the mineralized sutures in 1000 μg/mL of lysozyme solution as described in Example 3. The resulting lysozyme-incorporated mineralized sutures were then incubated at 37° C. in either 400 μL PBS buffer solution at pH 7.4 or 400 μL acetic acid buffer solution at pH 4.0. The release of lysozyme and calcium from the lysozyme-incorporated mineralized sutures was measured at various time points over 30 days. The amount of lysozyme remaining in the buffer solutions at each time point was assessed using Micro BCA protein assay (Pierce, Rockford, Ill.) and the amount of calcium in the buffer solutions at each time point was determined with a colorimetric assay using Arsenazo III. After measuring the amount of lysozyme and calcium in the buffer solutions at each time point, the buffer solutions were removed and replaced with fresh buffer solution. The results are shown in FIG. 5.

Figure 5A:
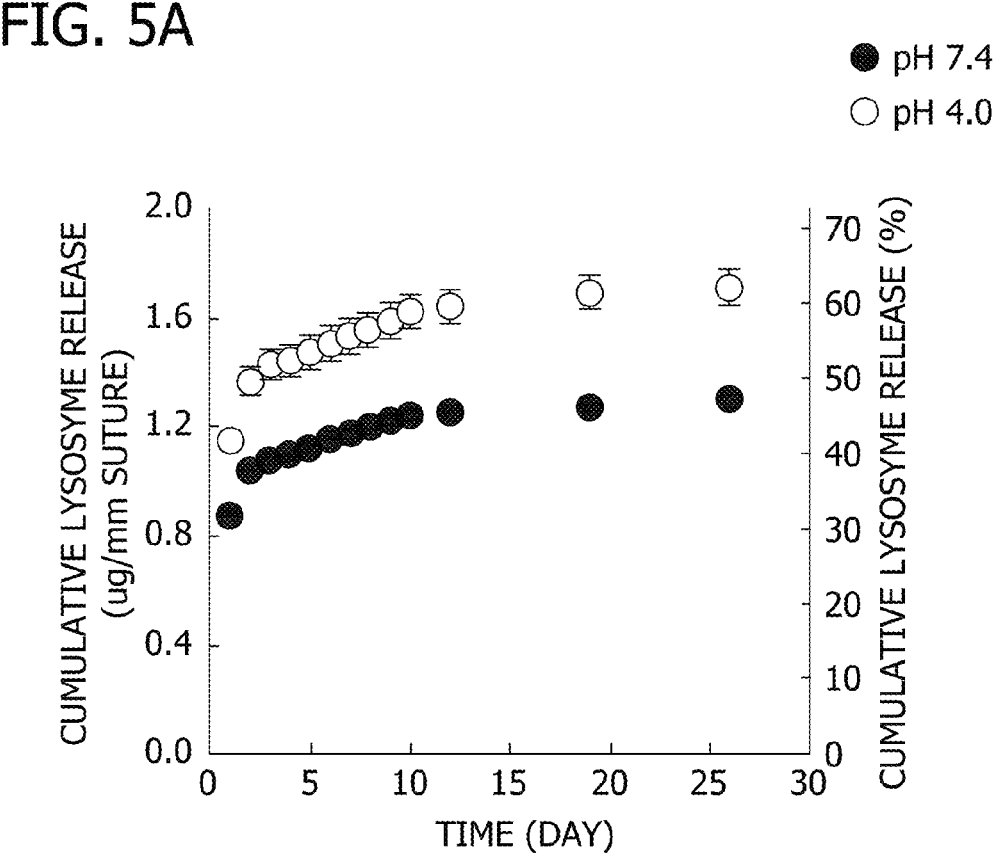
FIG. 5A is a chart showing the cumulative lysozyme release (μg/mm suture and % release) (average of 3; standard deviation n=3) from lysozyme-incorporated mineralized ORTHOCORD™ sutures in a pH 7.4 buffer solution (•) and in a pH 4.0 buffer solution (○), as discussed in Example 4.

FIG. 5A shows the cumulative lysozyme release (μg/mm suture and % release) (average of 3; standard deviation n=3) from the lysozyme-incorporated mineralized ORTHOCORD™ sutures in the pH 7.4 buffer solution (•) and in the pH 4.0 buffer solution (∘). As can be seen from FIG. 5A, the amount of release and release profile for lysozyme was significantly different depending on the external pH of the buffer solution. Lysozyme release was sustained over 30 days at pH 7.4 and completed in 20 days at pH 4.0. At both pH 7.4 and pH 4.0, abrupt release of lysozyme was observed until day 2 (50.0±2.0% at pH 4.0 and 38.2±0.7% at pH 7.4), and then steady release was observed thereafter for the next couple of weeks.

Figure 5B:
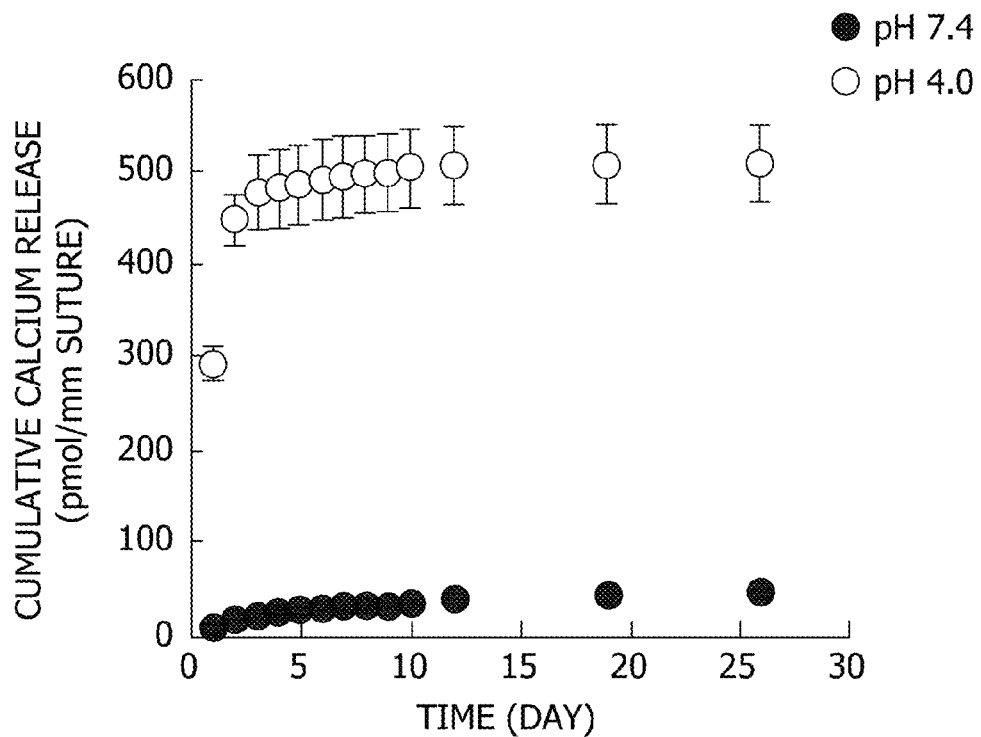
FIG. 5B is a chart showing the cumulative calcium release (pmol/mm suture) (average of 3; standard deviation n=3) from lysozyme-incorporated mineralized ORTHOCORD™ sutures in a pH 7.4 buffer solution (•) and in a pH 4.0 buffer solution (○), as discussed in Example 4.

FIG. 5B shows the cumulative calcium release (pmol/mm suture) (average of 3; standard deviation n=3) from the lysozyme-incorporated mineralized ORTHOCORD™ sutures in the pH 7.4 buffer solution (•) and in the pH 4.0 buffer solution (∘). Calcium release reflects dissolution of hydroxyapatite. As can be seen from FIG. 5B, the release profile for calcium was similar to that of lysozyme, except the differences caused by pH was more conspicuous for calcium. Acetic acid buffer at pH 4.0 caused rapid calcium release initially, bringing about 10-fold higher amount of released calcium than that from PBS at pH 7.4.

Figure 5C:
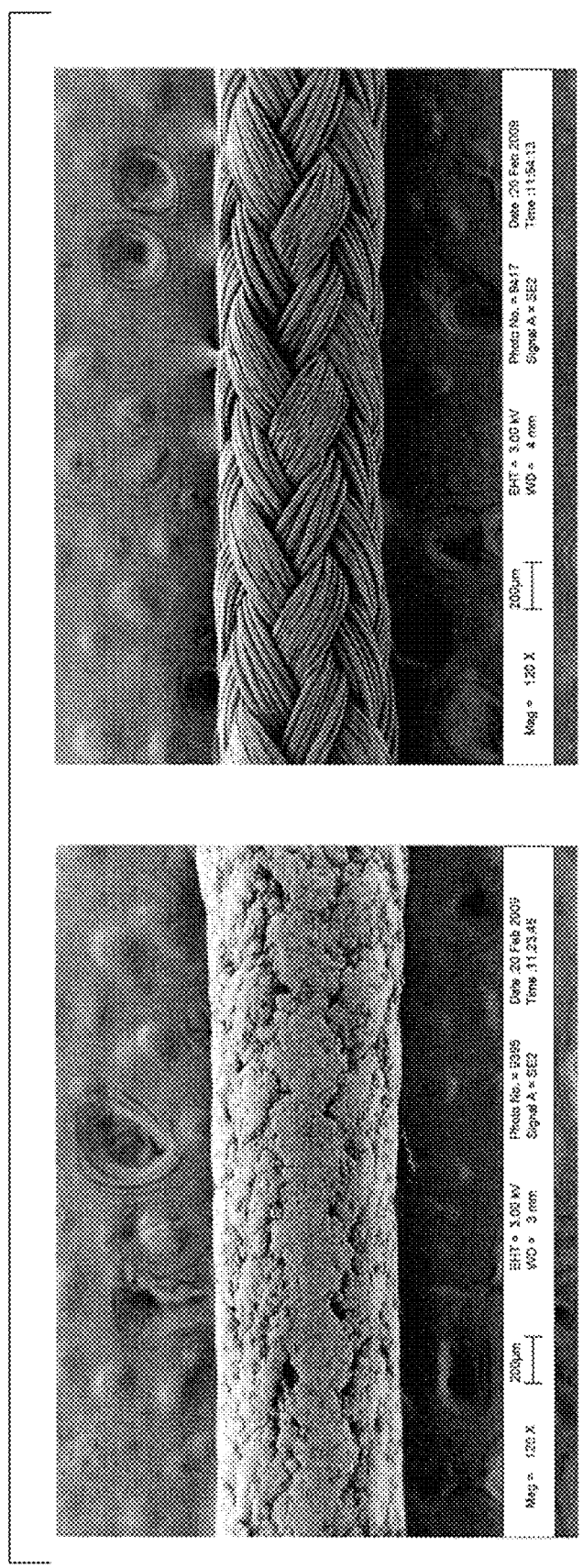
FIG. 5C is an SEM image of an ORTHOCORD™ suture taken after 33 days of incubation at pH 7.4 (first image) or pH 4.0 (second image), as discussed in Example 4.

Accelerated dissolution of calcium phosphate can also be confirmed from SEM images taken after 33 days of incubation using the LEO 1530 field-emission scanning electron microscopy (FE-SEM; Zeiss, Germany). These results are shown in FIG. 5C. As can be seen from FIG. 5C, after 33 days of incubation, there is negligible mineral debris present on the mineralized OrthoCord incubated at pH 4.0. In contrast, much of the mineralized hydroxyapatite layer is retained and uniformly covers the ORTHOCORD™ sutures incubated at pH 7.4.

Additionally, the lysozyme released from the lysozyme-incorporated mineralized OrthoCord sutures retained over 90% of its bioactivity after in vitro release, implying that the protein incorporation procedure used herein and binding with hydroxyapatite does not induce serious protein denaturation. It should be noted that the lysozyme bioactivity was measured using its lytic activity against the *Micrococcus lysodeikticus* according to the reported method of Helal, R., et al., "Determination of lysozyme activity by a fluorescence technique in comparison with the classical turbidity assay," Pharmazie, 2008, vol. 63, pp. 415-419.

Example 5

In this example, the stability of the hydroxyapatite layer on ORTHOCORD™ sutures was evaluated. Specifically, the binding strength between the polymeric suture surface and the hydroxyapatite layer, when subjected to friction similar to that occurring during the suturing procedure, was tested.

Mineralized sutures, prepared as described in Example 1 (60 minute hydrolysis), were passed through either the meniscus (a relatively tough, dense fibrocartilage) or the infraspinatus tendon (a component of the rotator cuff) of young sheep. After the sutures were passed through the tissue either two, five, or ten different times, the mineral coverage on the surface of the sutures before and after passage through the meniscus or infraspinatus tendon was observed by the naked eye. The results are shown in FIGS. 6A and 6B.

Figure 6A:
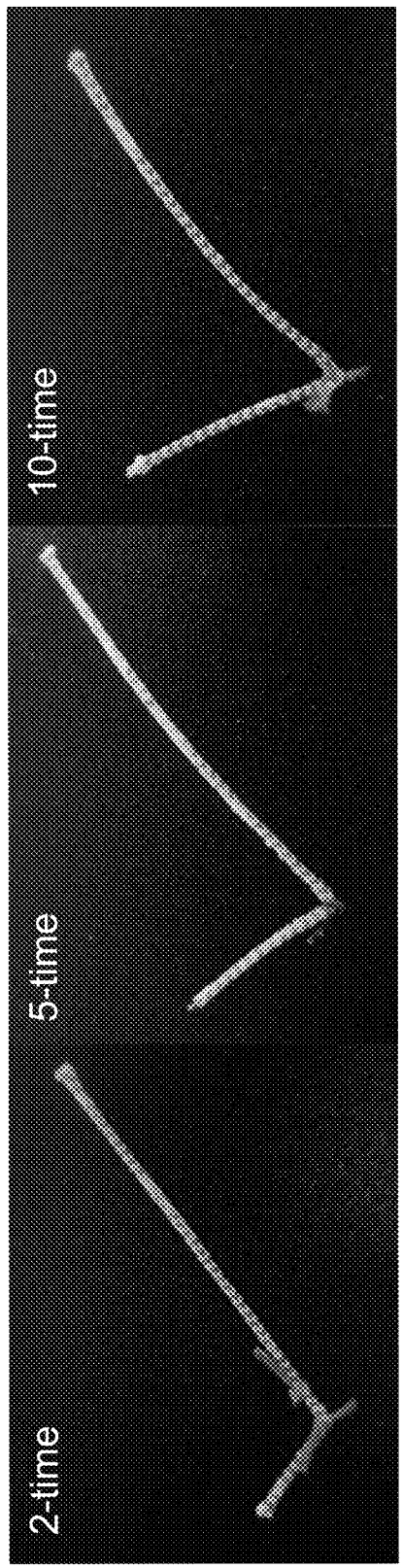
FIGS. 6A and 6B are photographs depicting hydroxyapatite-coated ORTHOCORD™ sutures after passing either two, five, or ten times through meniscus (FIG. 6A) or infraspinatus tendon (FIG. 6B), as discussed in Example 5.
Figure 6B:
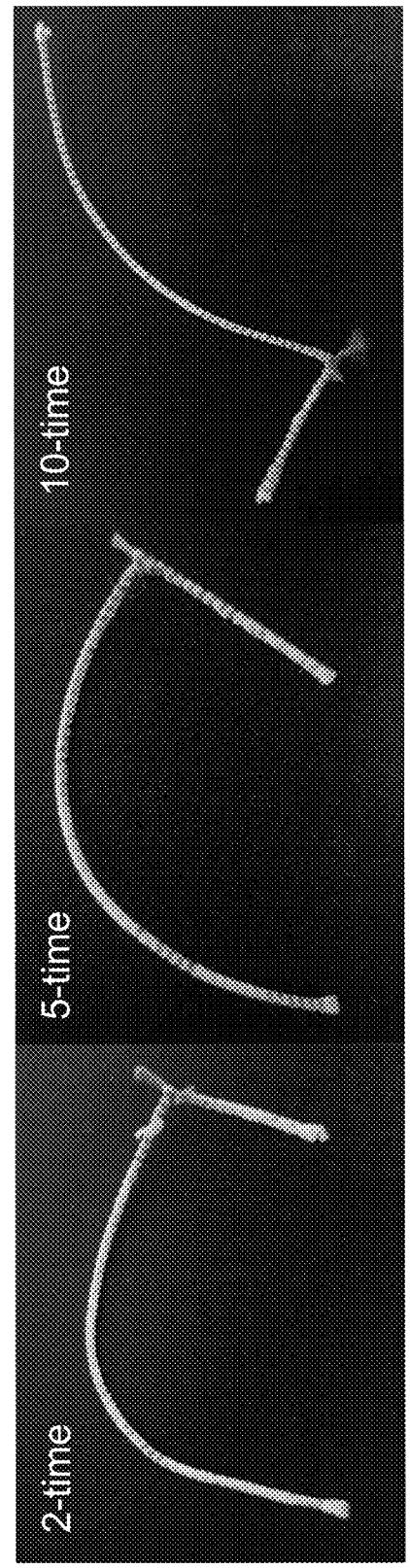

FIGS. 6A-6B are photographs depicting hydroxyapatite-coated ORTHOCORD™ sutures after passing either two, five, or ten passes through meniscus (FIG. 6A) or infraspinatus tendon (FIG. 6B). For both types of tissue, the hydroxyapatite layer retained and still covered most of the suture after passing through the tissue five times, but considerable portions of the hydroxyapatite coating appeared to be separated and removed from the sutures after passing through the tissue ten times.

For qualitative estimation of how much lysozyme remains after passage of the mineralized sutures through the infraspinatus tendon, the pass-through test was repeated using mineralized sutures containing rhodamine-labeled lysozyme. To perform this test, lysozyme-incorporated mineralized sutures were prepared as described in Example 4, except the lysozyme incorporated into the mineral layer was labeled with fluorescently active rhodamine. The sutures were passed through the infraspinatus tendon of young sheep six different times. The presence and qualitative amount of protein present on the suture after passing through the infraspinatus was estimated by comparing the fluorescence intensity before and after each pass through. The results are shown in FIG. 7.

Figure 7:
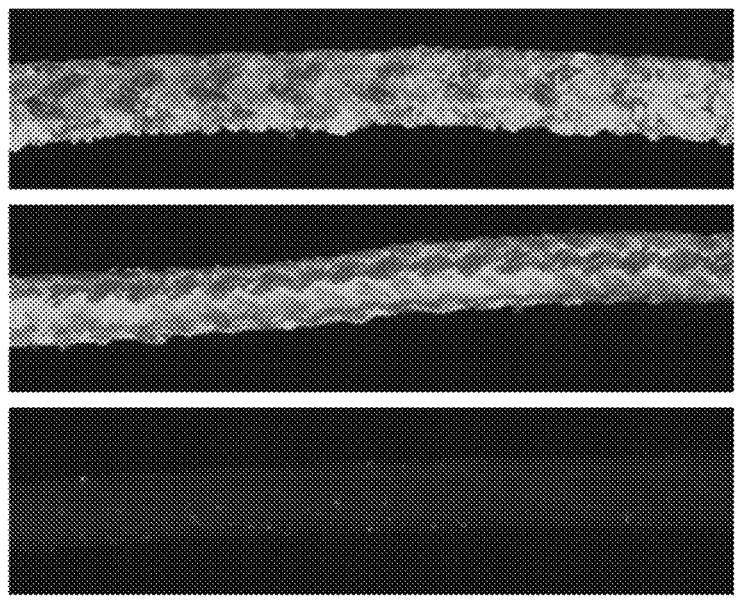
FIG. 7 shows fluorescence micrographs of rhodamine-conjugated lysozyme incorporated into hydroxyapatite-coated ORTHOCORD™ sutures before (top) and after (middle) six passes through the infraspinatus tendon of young sheep, as well a fluorescence micrograph of a non-mineralized ORTHOCORD™ suture after a four hour incubation in rhodamine-conjugated lysozyme solution (bottom), as discussed in Example 5.

FIG. 7 shows fluorescence micrographs of the rhodamine-conjugated lysozyme incorporated into the hydroxyapatite-coated ORTHOCORD™ sutures before (top) and after (middle) six passes through the infraspinatus tendon of young sheep, as well a fluorescence micrograph of a non-mineralized ORTHOCORD™ suture after a four hour incubation in rhodamine-conjugated lysozyme solution (bottom). As can be seen in FIG. 7, fluorescence intensity from the rhodamine-labeled lysozyme was maintained without any noticeable decrease after six tissue penetrations, even though the loss of the outer layer of hydroxapatite on the suture occurred to a certain extent. Although the hydroxyapatite coverage varied from region to region after passing the suture through the tissue, similar levels of fluorescence were detected over the entire suture. Without wishing to be bound to any particular theory, it is possible that the lysozyme proteins penetrated and were bound deep inside the porous hydroxyapatite coating layer, but not on the suture surface. The suture, therefore, still possessed significant amounts of proteins even after losing some of the outer layer of hydroxyapatite.

Example 6

Figure 8:
FIG. 8 is a photograph of a knotted suture comprising a hydroxyapatite layer on the surface thereof, as discussed in Example 6.

In this example, the flexibility of sutures having a hydroxyapatite layer coated thereon was demonstrated. A hydroxyapatite-coated OrthoCord suture, prepared as described in Example 1 (60 minute hydrolysis), was knotted. A photograph of the knotted suture is shown in FIG. 8. FIG. 8 demonstrates that the presence of the hydroxyapatite layer does not negatively impact the flexibility and knot-ability of the suture, and shows that sutures comprising a hydroxyapatite layer on the surface thereof have knot retention.

Example 7

In this example, the feasibility of spatially controlling the incorporation of proteins into a hydroxyapatite layer on the surface of a suture was demonstrated. Specifically, to demonstrate spatial control over protein incorporation, mineralized sutures were prepared using two fluorescently tagged proteins incorporated into the mineralized sutures in two different spatial orientations.

Figure 9B:
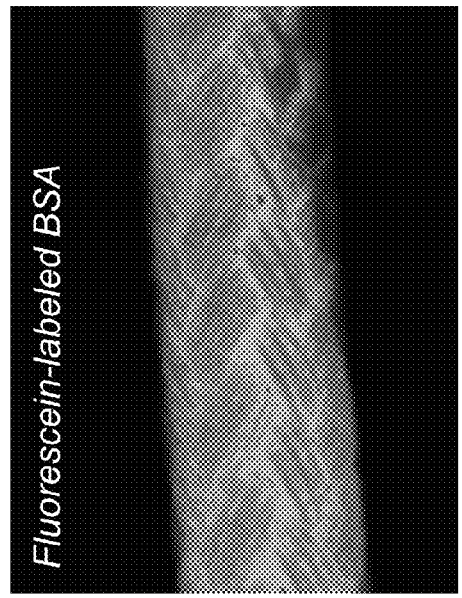
FIG. 9B is a fluorescence micrograph of the suture in FIG. 9A showing the presence of the fluorescein-labeled BSA.
Figure 9C:
FIG. 9C is a fluorescence micrograph of the suture in FIG. 9A showing the presence of the rhodamine-labeled lysozyme.
Figure 9A:
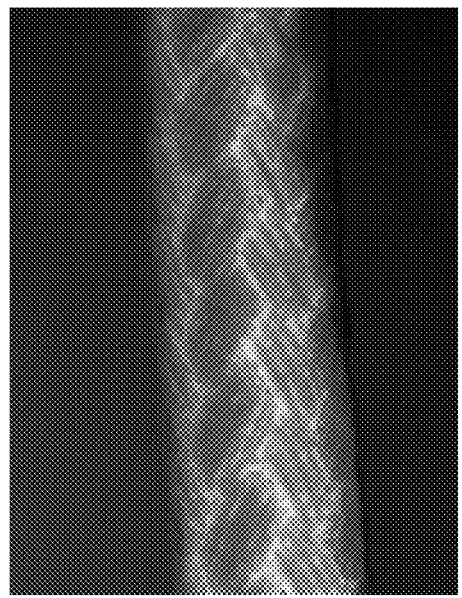
FIG. 9A is a micrograph of the suture.

Mineralized sutures containing two different proteins simultaneously in the same region of the suture were prepared. Mineralized ORTHOCORD™ sutures, prepared as described in Example 1 (60 minute hydrolysis), were dipped in fluorescein-labeled bovine serum albumin (BSA) solution (1 mg/mL) for less than about 1 minute, rinsed with water, and then dipped in rhodamine-labeled lysozyme solution (1 mg/mL). The resulting suture is shown in FIG. 9. FIG. 9 shows fluorescence micrographs taken from a single suture sequentially dipped into fluorescein-labeled BSA and rhodamine-conjugated lysozyme. FIG. 9A is a micrograph of the suture. FIG. 9B is a fluorescence micrograph of the suture in FIG. 9A showing the presence of the fluorescein-labeled BSA. FIG. 9C is a fluorescence micrograph of the suture in FIG. 9A showing the presence of the rhodamine-labeled lysozyme. As can be seen from FIG. 9, after dipping mineralized ORTHOCORD™ sutures into fluoroescein-labeled BSA and rhodamine-conjugated lysozyme sequentially, the suture can carry both proteins simultaneously on the same region.

Figure 10:
FIG. 10 is a fluorescence micrograph of a mineralized suture to which fluorescein-labeled BSA and the rhodamine-labeled lysozyme were applied in alternating locations on the suture, as discussed in Example 7.
Figure 11:
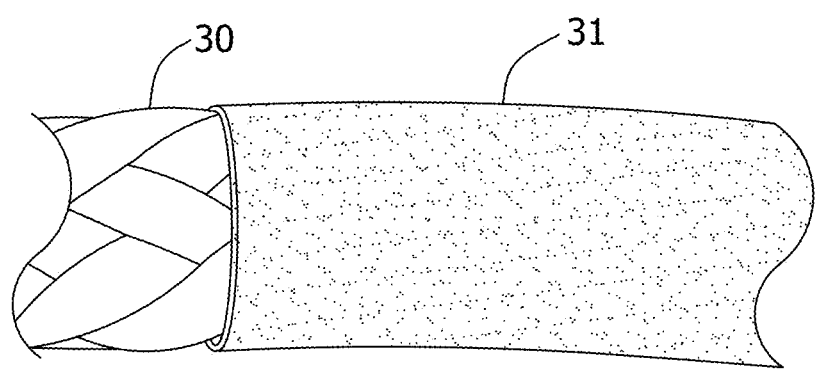
FIG. 11 is a schematic illustrating a mineralized suture depicting the suture material (30) and the mineral layer coating (31) associated with the surface of the suture material.

Mineralized sutures containing two different proteins in different regions of the suture were also prepare. The flourescein-labeled BSA and rhodamine-labeled lysozyme solutions described above were applied (via pipette) alternately to mineralized ORTHOCORD™ sutures (prepared as described in Example 1 with 60 minute hydrolysis). A fluorescence micrograph of the resulting suture is shown in FIG. 10. As can be seen from FIG. 10, the fluorescein-labeled BSA and the rhodamine-labeled lysozyme were in alternating locations on the suture, illustrating that a suture can be tailored to load two different proteins alternatively onto the suture with spatial control.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. A biologically active suture comprising:
    a suture material comprising one or more filaments, wherein a surface of the suture material is chemically hydrolyzed and comprises heterogeneous mineral nucleation sites thereon;
    at least one degradable mineral layer associated with the surface of the suture material; and
    at least one biological substance associated with the degradable mineral layer.

2. The suture of claim 1 wherein the suture material is bioresorbable.

3. The suture of claim 1 wherein the degradable mineral layer comprises a mineral selected from the group consisting of hydroxyapatite, α-tricalcium phosphate, β-tricalcium phosphate, amorphous calcium phosphate, dicalcium phosphate, octacalcium phosphate, calcium carbonate, calcium sulfate, and combinations thereof.

4. The suture of claim 1 comprising at least a first biological substance and a second biological substance.

5. The suture of claim 4 wherein the first biological substance and the second biological substance are associated with the same region of the degradable mineral layer.

6. The suture of claim 4 wherein the first biological substance and the second biological substance are associated with different regions of the degradable mineral layer.

7. The suture of claim 6 wherein the different regions are alternating regions.

8. The suture of claim 1 wherein the suture comprises a first degradable mineral layer associated with the surface of the suture material and at least a second degradable mineral layer associated with a surface of the first degradable mineral layer.

9. The suture of claim 8 wherein the at least one biological substance is associated with the first degradable mineral layer, the second degradable mineral layer, or combinations thereof.

10. The suture of claim 8 wherein the second degradable mineral layer is not associated with a biological substance.

* * * * *